(12) United States Patent
Frendeus et al.

(10) Patent No.: US 10,191,049 B2
(45) Date of Patent: Jan. 29, 2019

(54) SCREENING METHODS AND USES THEREOF

(71) Applicant: BioInvent International AB, Lund (SE)

(72) Inventors: Bjorn Frendeus, Landskrona (SE); Jenny Mattsson, Loddekopinge (SE)

(73) Assignee: BioInvent International AB, Lund (SE)

( * ) Notice: Subject to any disclaimer, the term of this patent is extended or adjusted under 35 U.S.C. 154(b) by 195 days.

(21) Appl. No.: 14/346,432

(22) PCT Filed: Sep. 20, 2012

(86) PCT No.: PCT/EP2012/068576
§ 371 (c)(1),
(2) Date: Mar. 21, 2014

(87) PCT Pub. No.: WO2013/041643
PCT Pub. Date: Mar. 28, 2013

(65) Prior Publication Data
US 2014/0227249 A1    Aug. 14, 2014

(30) Foreign Application Priority Data
Sep. 22, 2011   (GB) .................................. 1116364.9

(51) Int. Cl.
*G01N 33/48*     (2006.01)
*G01N 33/566*    (2006.01)
*G01N 33/68*     (2006.01)
*C12N 15/10*     (2006.01)
*G06G 7/58*      (2006.01)

(52) U.S. Cl.
CPC ....... *G01N 33/566* (2013.01); *C12N 15/1037* (2013.01); *G01N 33/6845* (2013.01); *G01N 33/6857* (2013.01); *G01N 2500/00* (2013.01)

(58) Field of Classification Search
None
See application file for complete search history.

(56) References Cited

U.S. PATENT DOCUMENTS

| 5,366,862 A | 11/1994 | Venton et al. |
| 5,688,507 A | 11/1997 | Weitz et al. |
| 6,794,128 B2 | 9/2004 | Marks et al. |
| 7,135,287 B1 | 11/2006 | Lonberg et al. |
| 8,592,347 B2 | 11/2013 | Frendeus |
| 2014/0200152 A1 | 7/2014 | Frendeus |
| 2016/0312383 A1 | 10/2016 | Frendeus |

FOREIGN PATENT DOCUMENTS

| CN | 101333243 A | 12/2008 |
| CN | 101939333 A | 1/2011 |
| GB | 2392723 B | 1/2005 |
| WO | WO-91/18980 | 12/1991 |
| WO | WO-91/189800 A1 | 12/1991 |
| WO | WO-2000/052054 A2 | 9/2000 |
| WO | WO-2002/039120 A1 | 5/2002 |
| WO | WO-2004/023140 A1 | 3/2004 |
| WO | WO-2004/101790 A1 | 11/2004 |
| WO | WO-2009/079793 A1 | 7/2009 |
| WO | 2013/041643 A1 | 3/2013 |

OTHER PUBLICATIONS

Barbas et al., "Assembly of combinatorial antibody libraries on phage surfaces: The gene III site", *Proc. Natl. Acad. Sci. USA*, 88:7978-7982 (1991).
Beck et al., "Strategies and challenges for the next generation of therapeutic antibodies", *Nat. Rev. Immunol.*, 10:345-352 (2010).
Beers et al., "Type II (tositumomab) anti-CD20 monoclonal antibody out performs type I (rituximab-like) reagents in B-cell depletion regardless of complement activation", *Blood*, 112(10):4170-4177 (2008).
Bentley et al., "Accurate Whole Human Genome Sequencing using Reversible Terminator Chemistry", *Nature*, 456:53-59 (2008).
Carlsson et al., "Binding of Staphylococcal Enterotoxin A to Accessory Cells is a Requirement for its Ability to Activate Human T Cells", *J. Immunol.*, 140:2484-2488 (1988).
Chiswell and McCafferty, "Phage antibodies will new 'coliclonal' antibodies replace monoclonal antibodies?" *Trends Biotechnol.*, 10:80-84 (1992).
Clackson et al., "Making antibody fragments using phage display libraries", *Nature*, 352:624-628 (1991).
Cragg and Glennie, "Antibody specificity controls in vivo effector mechanisms of anti-CD20 reagents", *Blood*, 103(7):2738-2743 (2004).
De Kruif et al., "Rapid selection of cell subpopulation-specific human monoclonal antibodies from a synthetic phage antibody library", *Proc. Natl. Acad. Sci. USA*, 92:3938-3942 (1995).
Drmanac et al., Human Genome Sequencing Using Unchained Base Reads on Self-Assembling DNA Nanoarrays, *Science*, 327:78-81 (2010).
Felici et al., "Peptide and protein display on the surface of filamentous bacteriophage", *Biotechnology Annual Review*, 1:149-183 (1995).
Francisco et al., "Specific Adhesion and Hydrolysis of Cellulose by Intact *Escherichia coli* Expressing Surface Anchored Cellulase or Cellulose Binding Domains", *Biotechnology*, 11:491-495 (1993).
Fransson et al., "Rapid induction of apoptosis in B-cell lymphoma by functionally isolated human antibodies", *Int. J. Cancer.*, 119:349-358 (2006).
Gao et al., "Making chemistry selectable by linking it to infectivity", *Proc. Natl. Acad. Sci. USA*, 94:11777-11782 (1997).

(Continued)

*Primary Examiner* — Eric S Dejong
(74) *Attorney, Agent, or Firm* — McCarter & English, LLP; Steven G. Davis; Yu Lu

(57) ABSTRACT

The present invention relates to improved screening methods and, in particular, to methods of screening anti-ligand libraries for identifying anti-ligands specific for differentially and/or infrequently expressed ligands.

21 Claims, 10 Drawing Sheets

(56) References Cited

OTHER PUBLICATIONS

Figure 1:
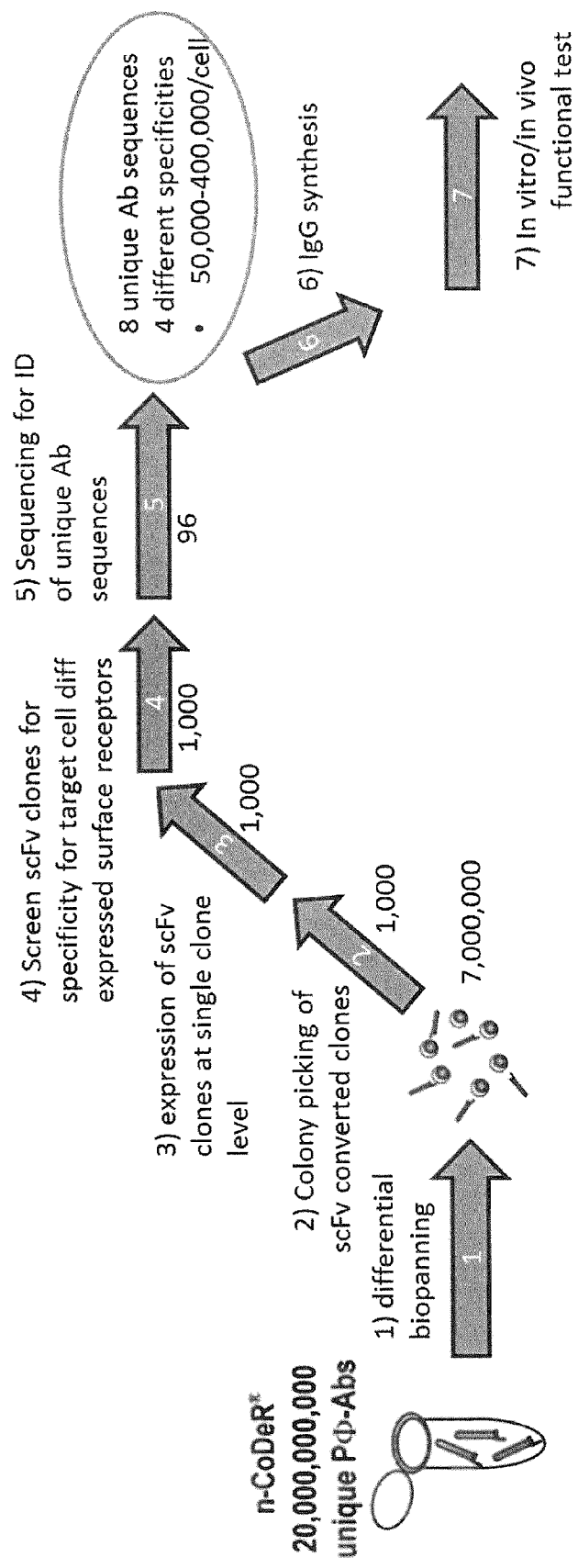

Hanes and Pluckthun, "In vitro selection and evolution of functional proteins by using ribosome display", *Proc. Natl. Acad. Sci. USA*, 94:4937-4942 (1997).

Harris et al., Single-Molecule DNA Sequencing of a Viral Genome, *Science*, 320:106-109 (2008).

He and Taussig, "Antibody-ribosome-mRNA (ARM) complexes as efficient selection particles for in vitro display and evolution of antibody combining sites", *Nucleic Acids Research*, 25(24):5132-5134 (1997).

Hoogenboom and Winter, By-passing Immunisation: Human Antibodies from Synthetic Repertoires of Germline $V_H$ Gene Segments Rearranged in Vitro, *J. Mol. Biol.*, 227:381-388 (1992).

Hoogenboom et al., "Antibody phage display technology and its applications", *Immunotechnology*, 4(1):1-20 (1998).

Hoogenboom, "Overview of Antibody Phage Display Technology and Its Applications," *Methods in Molecular Biology*, O'Brien, and Aitken, eds. (Totowa, NJ: Humana Press Inc.), pp. 1-37 (2002).

Huls et al., "A recombinant, fully human monoclonal antibody with antitumor activity constructed from phage-displayed antibody fragments," *Nature Biotechnology*, 17:276-281 (1999).

Jacobsson and Frykberg, "Cloning of Ligand-Binding Domains of Bacterial Receptors by Phage Display", *Biotechniques*, 18(5):878-885 (1995).

Katz, "Structural and Mechanistic Determinants of Affinity and Specificity of Ligands Discovered or Engineered by Phage Display", *Annual Rev. Biophys. Biomol. Struct.*, 26:27-45 (1997).

Kay and Paul, "High-throughput screening strategies to identify inhibitors of protein-protein interactions", *Molecular Diversity*, 1:139-140 (1995).

Koide et al., "The Fibronectin Type III Domain as a Scaffold for Novel Binding Proteins", *J. Mol. Biol.*, 284:1141-1151 (1998).

Liu et al., "Mapping Tumor Epitope Space by Direct Selection of Single-Chain Fv Antibody Libraries on Prostate Cancer Cells," *Cancer Research*, 64:704-710 (2004).

Lou et al., "Antibodies in haystacks: how selection strategy influences the outcome of selection from molecular diversity libraries", *Journal of Immunological Methods*, 253:233-242 (2001).

Lundquist et al., "Parallel confocal detection of single molecules in real time", *Optics Letters*, 33(9):1026-1028 (2008).

Mandecki et al., "A Mathematical Model for Biopanning (Affinity Selection) Using Peptide Libraries on Filamentous Phage". *J. Theor. Biol.*, 176:523-530 (1995).

Margulies et al., "Genome Sequencing in Open Microfabricated High Density Picoliter Reactors", *Nature*, 437(7057):376-380 (2005).

Markland et al., Design, construction and function of a multicopy display vector using fusions to the major coat protein of bacteriophage M13, *Gene*, 109:13-19 (1991).

Marks et al., "By-passing Immunization: Human Antibodies from V-gene Libraries Displayed on Phage", *J. Mol. Biol.*, 222:581-597 (1991).

Mattheakis et al., "An in vitro polysome display system for identifying ligands from very large peptide libraries", *Proc. Natl. Acad. Sci. USA*, 91:9022-9026 (1994).

McCafferty et al., Phage antibodies: filamentous phage displaying antibody variable domains:, *Nature*, 348:552-554 (1990).

Mutuberria et al., "Model systems to study the parameters determining the success of phage antibody selections on complex antigens", *J. Immunol. Methods*, 237:65-81 (1999).

Osbourn et al., "Pathfinder selection: in situ isolation of novel antibodies", *Immunotechnology*, 3:293-302 (1998).

Pluckthun et al., "In Vitro Selection and Evolution of Proteins", *Adv. Chem.*, 55:367-403 (2001).

Ravn et al., "By-passing in vitro screening—next generation sequencing technologies applied to antibody display and in silico candidate selection", *Nucleic Acids Research*, 38(21):e193 (2010).

Rodi et al., "Screening of a Library of Phage-displayed Peptides Identifies Human Bcl-2 as a Taxol-binding Protein", *J. Mol. Biol.*, 285:197-203 (1999).

Schwab and Bosshard, "Caveats for the use of surface-adsorbed protein antigen to test the specificity of antibodies", *J. Immunol. Methods*, 147:125-134 (1992).

Shendure et al., "Accurate Multiplex Polony Sequencing of an Evolved Bacterial Genome", *Science*, 309:1728-1732 (2005).

Siegel et al., "Isolation of cell surface-specific human monoclonal antibodies using phage display and magnetically-activated cell sorting: applications in immunohematology", *J. Immunol. Methods*, 206:73-85 (1997).

Smith, George P., "Filamentous Fusion Phage: Novel Expression Vectors That Display Cloned Antigens on the Virion Surface", *Science*, 228:1315-1317 (1985).

Smith and Scott, "Libraries of Peptides and Proteins Displayed on Filamentous Phage", *Methods Enzymol.*, 217:228-257 (1993).

Stahl et al., A dual expression system for the generation, analysis and purification of antibodies to a repeated sequence of the Plasmodium falciparum antigen Pf155/RESA, *J. Immunol. Methods*, 124:43-52 (1989).

Stausbol-Gron et al., "A model phage display subtraction method with potential for analysis of differential gene expression", *FEBS Letters*, 391:71-75 (1996).

Stausbol-Gron et al., "De novo identification of cell-type specific antibody-antigen pairs by phage display subtraction", *Eur. J. Biochem.*, 268:3099-3107 (2001).

Weng et al., Generating addressable protein microarrays with PROfusion™ covalent mRNA-protein fusion technology, *Proteomics*, 2:48-57 (2002).

Williams and Sharon, "Polyclonal anti-colorectal cancer Fab phage display library selected in one round using density gradient centrifugation to separate antigen-bound and free phage", *Immunology Letters*, 81:141-148 (2002).

Winter and McCafferty, *Phage Display of Peptides and Proteins: A Laboratory Manual*, Ed. Kay, Academic Press, Inc. ISBN 0-12-402380-0 (1996).

Winter et al., Making Antibodies by Phage Display Technology, *Annu. Rev. Immunol.*, 12:433-455 (1994).

Zhang et al., "Phenotype-information-phenotype cycle for deconvolution of combinatorial antibody libraries selected against complex systems", *Proc. Natl. Acad. Sci. USA*, 108(33):13456-13461 (2011).

Yu et al. "High-fluxed DNA Sequencing Technology and Its Application Development", J Nanjing Xiaozhuang University, 3:1-5 (2010).

Glanville et al., "Precise determination of the diversity of a combinatorial antibody library gives insight into the human immunglobulin repertoire," *PNAS*, 106(48):20216-20221 (2009).

Reddy et al., "Monoclonal antibodies isolated wthout screening by analyzing the variable-gene repertoire of plasma cells," *Nature Biotech.*, 28(9):965-969 (2010).

Wang et al., "Prospects of clinical application of new generational high flux sequencing technique," *Guangdong Medical J.*, 3:269-272 (2010).

"Cost per Raw Megabase of DNA Sequence," graph and table of sequencing costs from www.genome.gov/sequencingcosts, National Human Genmoe Research Institute (2014).

CN 101333243 English abstract.

CN 101939333 English abstract.

Kay et al., "Principles and Applications of Phage Display," Phage Display of Peptides and Proteins: A Laboratory Manual, Kay (ed.), Academic Press, Inc. (1996) ISBN 0-12-402380-0, Chapter 10, pp. 21-189.

scienceworld.wolfram.com, "Law of Mass Action," 3 pages, printed Mar. 10, 2010.

Ravn U. et al, "By-passing in vitro screening—next generation sequencing technologies applied to antibody display and in silico candidate selection"; Nucleic Acids Research, 2010, vol. 38. No. 21, e193.

Fischer, "Sequencing antibody repertoires—The next generation"; mAbs 3:1, 17-20 (Jan./Feb 2011).

Shinohara et al, "Isolation of a vascular cell wall-specific monoclonal antibody recognizing a cell polarity by using a phage display subtraction method", PNAS, 97(6):2585-2590, 2000.

Boel, E., et al, "Phage Antibodies Obtained by Competitive Selection on Complement-Resistant Moraxella (Branhamella) catarrhalis

(56) References Cited

OTHER PUBLICATIONS

Recognize the High-Molecular-Weight Outer Membrane Protein", Infection and Immunity, vol. 66(1):83-88, 1998.
Shionhara, N., et al., "Isolation of monoclonal antibodies recognizing rare and dominant epitopes in plant vascular cell walls by phage display subtraction", Journal of Immunological Methods, 264:187-194, 2002.
Ballard et al., Quantitative PCR-based approach for rapid phage display analysis: a foundation for high throughput vascular proteomic profiling. Physiol Genomics. Aug. 16, 2006;26(3):202-8.
Dias-Neto et al., Next-generation phage display: integrating and comparing available molecular tools to enable cost-effective high-throughput analysis. PLoS One. Dec. 17, 2009;4(12):e8338.
Oxford English Dictionary. Ligand. Retrieved online at: https://en.oxforddictionaries.com/definition/ligand. 1 page.
Sadava et al., Life: The Science of Biology, Ninth Edition. Sinauer Associates, Inc., Sunderland, MA. pp. 369-370 (2011).
Liu et al., Efficient Identification of Murine M2 Macrophage Peptide Targeting Ligands by Phage Display and Next-Generation Sequencing. Bioconjug Chem. Aug. 19, 2015;26(8):1811-7.
Mandecki et al., A mathematical model for biopanning (affinity selection) using peptide libraries on filamentous phage. J Theor Biol. Oct. 21, 1995;176(4):523-30.
Peptalk, the Protein Science Week Brochure, Jan. 8-12, 2018. Emerging Technologies for Antibody Discovery, Exploring the Intersection of Display Technologies, Next-Generation Sequencing and Informatics for the Discovery of Next-Generation Biotherapeutics. 13 pages (2018).

Antigen expression on TAR/NOT cells

| Antigen type | Phagemid Specificity | Antigens/ TAR cell (tmp) | Antigens/ NOT cell (tmn) | Relative frequency |
|---|---|---|---|---|
| 1 | + Cell Restricted Antigen | 200 000 | 0 | 1 |
| 2 | + Cell Restricted Antigen | 50 000 | 0 | 1 |
| 3 | + Cell Restricted Antigen | 25 000 | 0 | 1 |
| 4 | + Cell Restricted Antigen | 5 000 | 0 | 1 |
| 5 | + Cell Enriched Antigen | 150 000 | 10 000 | 1 |
| 6 | + Cell Enriched Antigen | 50 000 | 10 000 | 1 |
| 7 | + Cell/ - Cell Commonly expressed antigen | 1 000 000 | 1 000 000 | 10 |
| 8 | + Cell/ - Cell Commonly expressed antigen | 500 000 | 500 000 | 10 |
| 9 | + Cell/ - Cell Commonly expressed antigen | 100 000 | 100 000 | 10 |
| 10 | + Cell/ - Cell Commonly expressed antigen | 50 000 | 50 000 | 10 |

Equation (VI) [1]
$bp += p/(A*V*Kd+(tmp*Cp+tmn*Cn))*(tmp*Cp)$

Selection parameters
Affinity Kd
| R1 | 3,00E-09 |
| R2 | 3,00E-01 |
| R3 | 2,00E+03 | scFv display freq./ phage
genotype/phenotype specific phage input R1
reaction volume V (L)
| R1 | 2,50E-03 |
| R2 | 5,00E-04 |
| R3 | 5,00E-04 |

No of cells used in selection rounds

| Selection round | TAR cells (Cp) | NOT cells (Cn) |
|---|---|---|
| R1 | 5,00E+07 | 2,00E+09 |
| R2 | 5,00E+06 | 1,00E+09 |
| R3 | 5,00E+06 | 1,00E+09 |

Amplification factor
(AF) R1-R2  1,50E+03
(AF) R2-R3  6,00E+04

Avogadro´s constant (A)  6,022E+23

Panning round

R1
| Type | Phage input (p) | Recovered (bp+) | Relative frequency |
|---|---|---|---|
| 1 | 6,00E+02 | 413 | 0,2650 |
| 2 | 6,00E+02 | 214 | 0,1371 |
| 3 | 6,00E+02 | 130 | 0,0834 |
| 4 | 6,00E+02 | 31 | 0,0202 |
| 5 | 6,00E+02 | 141 | 0,0901 |
| 6 | 6,00E+02 | 56 | 0,0356 |
| 7 | 6,00E+02 | 146 | 0,0936 |
| 8 | 6,00E+02 | 146 | 0,0934 |
| 9 | 6,00E+02 | 143 | 0,0918 |
| 10 | 6,00E+02 | 140 | 0,0899 |

R2
| Type | Phage input (p) | Recovered (bp+) | Relative frequency |
|---|---|---|---|
| 1 | 1,86E+05 | 9,77E+04 | 0,7404 |
| 2 | 9,62E+04 | 2,09E+04 | 0,1580 |
| 3 | 5,85E+04 | 7,12E+03 | 0,0539 |
| 4 | 1,42E+04 | 3,81E+02 | 0,0029 |
| 5 | 6,33E+04 | 4,07E+03 | 0,0308 |
| 6 | 2,50E+04 | 5,60E+02 | 0,0042 |
| 7 | 6,57E+03 | 3,27E+02 | 0,0025 |
| 8 | 6,56E+03 | 3,26E+02 | 0,0025 |
| 9 | 6,44E+03 | 3,18E+02 | 0,0024 |
| 10 | 6,31E+03 | 3,08E+02 | 0,0023 |

R3
| Type | Phage input (p) | Recovered (bp+) | Relative frequency |
|---|---|---|---|
| 1 | 1,76E+09 | 9,24E+08 | 0,9004 |
| 2 | 3,75E+08 | 8,14E+07 | 0,0793 |
| 3 | 1,28E+08 | 1,56E+07 | 0,0152 |
| 4 | 6,87E+06 | 1,85E+05 | 0,0002 |
| 5 | 7,33E+07 | 4,72E+06 | 0,0046 |
| 6 | 1,01E+07 | 2,26E+05 | 0,0002 |
| 7 | 5,88E+05 | 2,92E+04 | 0,0000 |
| 8 | 5,86E+05 | 2,91E+04 | 0,0000 |
| 9 | 5,72E+05 | 2,82E+04 | 0,0000 |
| 10 | 5,55E+05 | 2,71E+04 | 0,0000 |

Figure 2

A
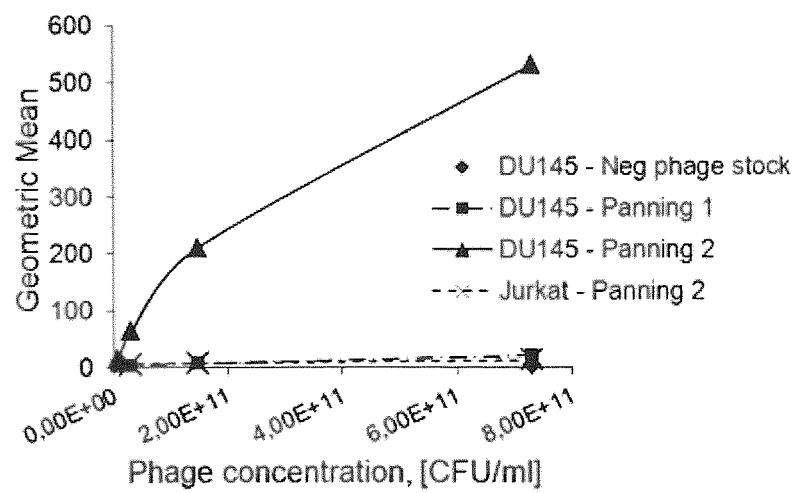
B
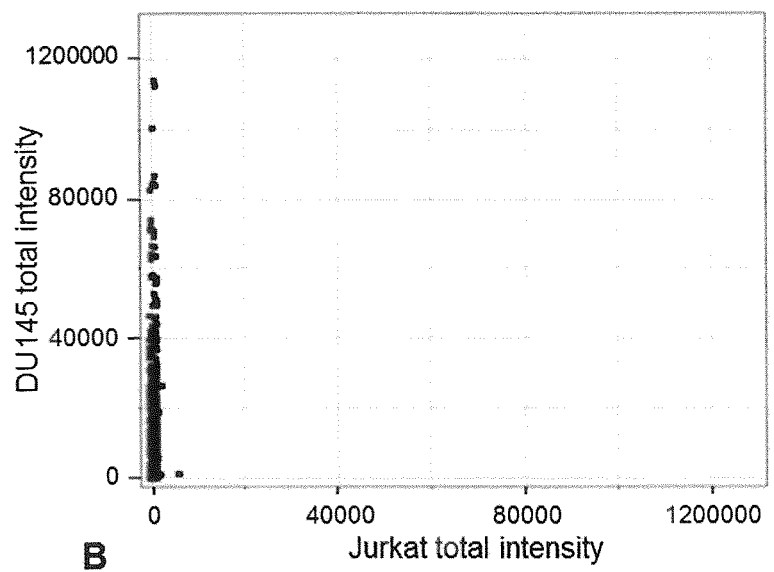
*Figure 3*

A
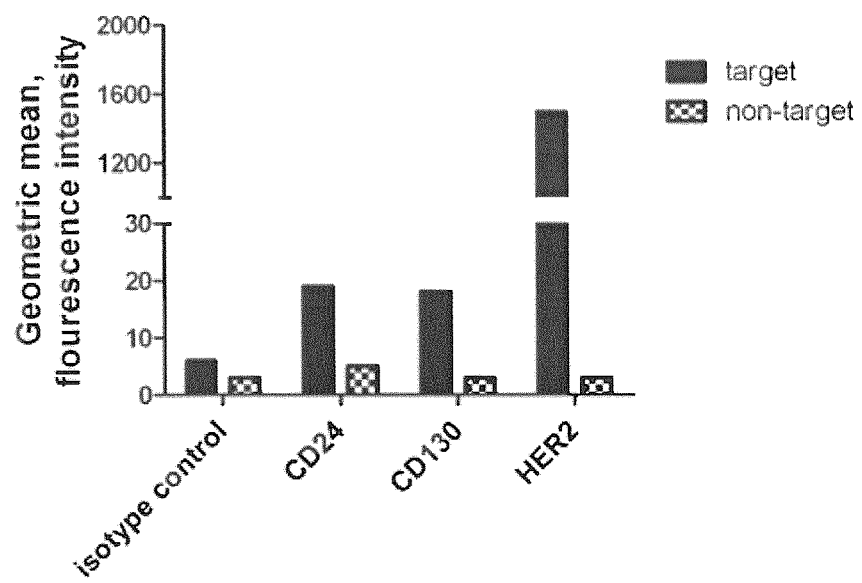
B
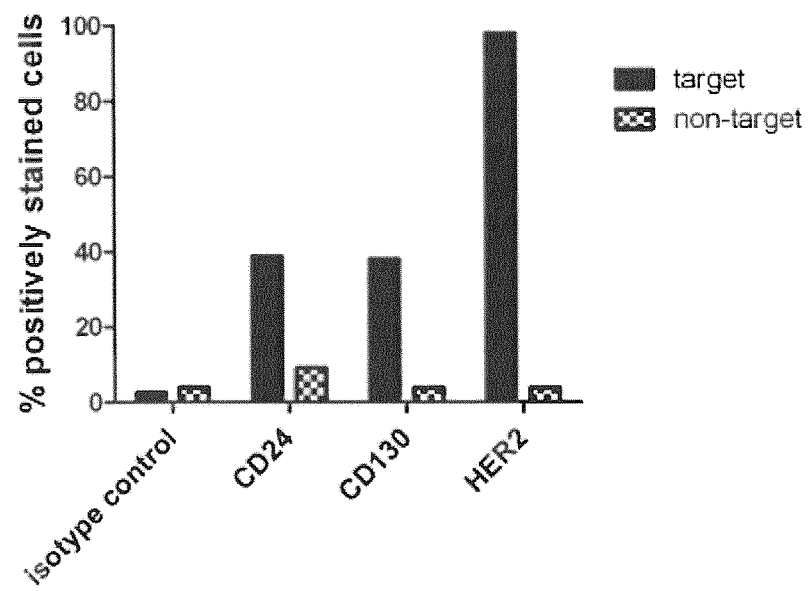
*Figure 4*

A
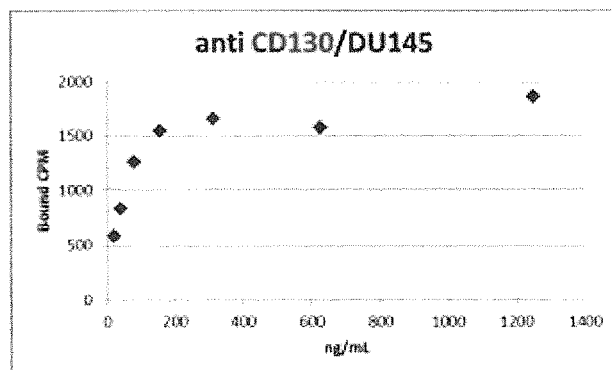
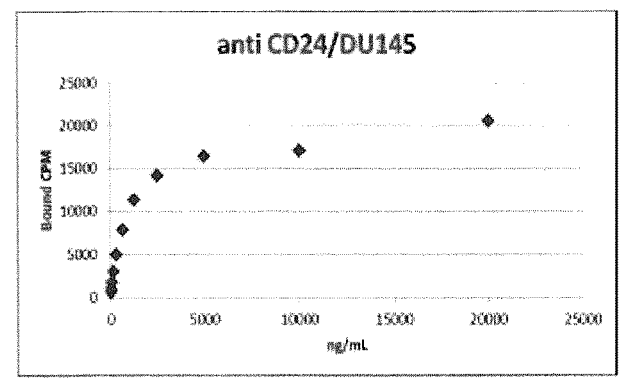
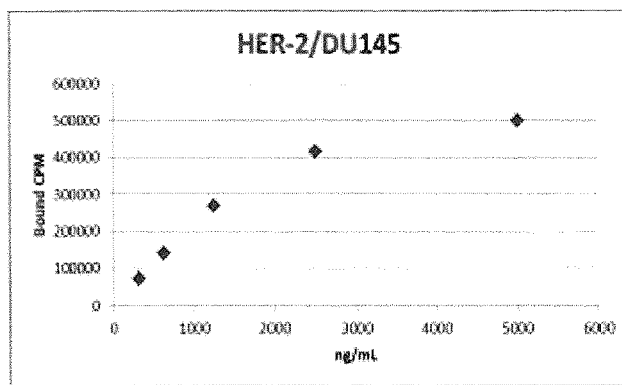
*Figure 5*

B
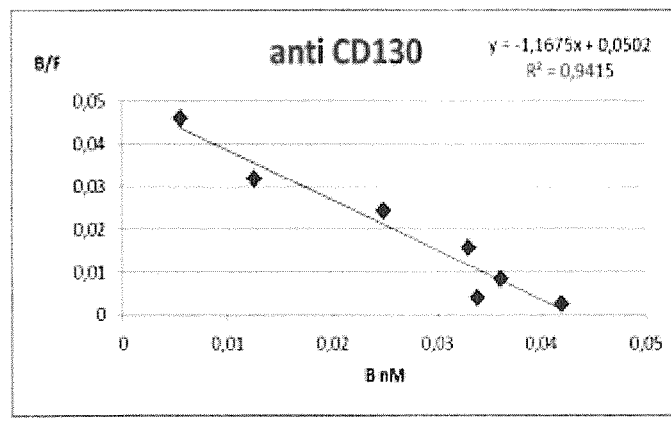
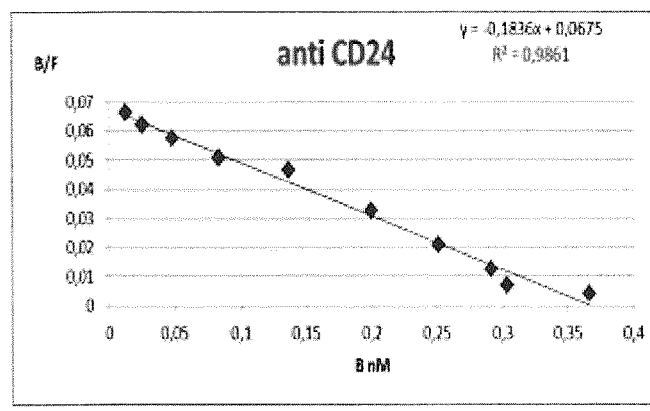
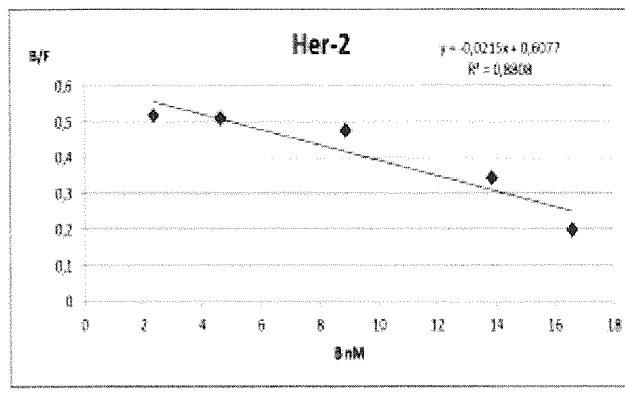
*Figure 5 (con't)*

SCREENING METHODS AND USES THEREOF

RELATED APPLICATIONS

This application is a 35 U.S.C. § 371 national stage filing of International Application No. PCT/EP2012/068576, filed Sep. 20, 2012, which claims priority to United Kingdom Patent Application No. 1116364.9, filed Sep. 22, 2011.

The present invention relates to improved screening methods and, in particular, to methods of screening anti-ligand libraries for identifying anti-ligands specific for differentially and/or infrequently expressed ligands.

Protein or peptide based libraries are often used for selection of anti-ligand molecules with specificity for certain ligands.

Such libraries are constructed so that the protein molecule is, in some manner, physically linked to the genetic information encoding the particular protein molecule. The protein molecule is thus displayed together with its gene.

Commonly used display formats rely on cell or virus host particles to present the protein molecule; and include bacterial display (Francisco et al., 1993) and phage display (Smith, 1985; Smith and Scott, 1993; Winter et al., 1994). Such systems display the potential anti-ligand molecule on the surface of the host particle, whilst the genetic information for the displayed molecule is harboured inside the particle and said methods have been employed successfully for selection of specific protein based anti-ligands.

Other display formats relying on in vitro translation exist; including various forms of ribosome display (Mattheakis et al., 1994; Hanes and Pluckthun, 1997; He and Taussig, 1997) that rely on non-covalent linkage of the genetic information to the protein molecule; and other display formats also relying on in vitro translation, whereby a covalent linkage exists between the genetic information and the potential anti-ligand protein molecule, e.g. the Profusion (Weng et al., 2002) or the Covalent Display Technology (Gao et al., 1997).

The displayed peptide or proteinaceous anti-ligand libraries may be totally randomised, e.g. when peptide libraries are used, or they may be based on a constant region scaffold structure incorporating a further structure conferring variability.

Scaffold structures often used are based on the antibody heavy and light chain variable domains (McCafferty et al., 1990) but may also be based on other scaffolds such as fibronectin (Jacobsson and Frykberg, 1995; Koide et al., 1998), protein A domains (Stahl et al., 1989), or small stable protein domains e.g. BPTI (Markland at al., 1991).

Selection of anti-ligands exhibiting a certain binding specificity, from display libraries, is often performed using so called "biopanning" methods.

The target ligand may be immobilised on a solid surface and specific anti-ligand members of a library are exposed to the immobilised target ligand to enable the anti-ligands of interest to bind to the target ligand. Unbound library members are subsequently washed away and the anti-ligands of interest are retrieved and amplified.

Proteinaceous particles other than the members of the anti-ligand library, e.g. phage expressing antibody fragments, may be "sticky" resulting in the binding and isolation of some non-target specific molecules. Non-specific binding may be minimised by adding certain compounds to the anti-ligand display construct/ligand mixture in order to act as blocking agents to reduce this background binding of non-specific anti-ligands e.g. milk, bovine serum albumin, serum (human/foetal calf), gelatine and for certain (non-cellular) applications, detergent.

A number of washing procedures have been devised to reduce non-specific binding of library members to cells and to aid separation of cells from contaminating and/or non-specifically bound library members.

Such methods include washing of cells magnetically fixed in a column (Siegel et al., 1997), in order to minimise shearing forces and to allow rebinding of dissociated phage. Another method of washing cells is by centrifugation in a higher density medium such as Ficoll or Percoll, in order to selectively remove non-specific and low affinity anti-ligands and further spatially separate cells and cell-bound anti-ligands from free-anti-ligands and non-specifically bound anti-ligands (Carlsson et al., 1988; Williams and Sharon, 2002).

Depending on the efficiency of the selection process, several rounds of panning may be required to eliminate or at least sufficiently reduce non-specific anti-ligands to a desirable level (Dower et al., 1991).

In another selection method, the target ligand(s) binds the specific anti-ligand library members whilst in solution. Bound anti-ligands are then isolated using, for example, a retrievable tag attached to the target ligand. The most commonly used tag is biotin, which permits the complex between target molecule and displayed specific library member to be retrieved using avidin coupled to a solid support e.g. a magnetic bead (Siegel et al., 1997).

These methods are used when the target ligand is well known and available in a purified form. Selections against a single target ligand at a time are routine. Selection for several defined target ligands may be performed simultaneously. Target ligands may be one or more of small haptens, proteins, carbohydrates, DNA and lipids.

For many applications, specific anti-ligands against differentially expressed ligands are of interest. For example, proteins may be differentially expressed on cells and tissue derived from patients with disease, when compared to those from healthy controls. Such diseases include microbial, viral, or parasitic infections, asthma, chronic inflammatory and autoimmune disorders, cancer, neurological-, cardiovascular-, or gastrointestinal disease. Similarly, the protein composition of body fluids, e.g. plasma, cerebrospinal fluid, urine, semen, saliva and mucous, may differ between patients with disease compared to healthy controls.

Consequently, besides their general applicability as research tools to identify differentially expressed ligands, anti-ligands specific for differentially expressed ligands may be used as tools for use in the diagnosis, prevention and/or treatment of disease.

Recent advances within the genomics and proteomics fields have indicated the presence of a multitude of as yet undefined differentially expressed molecules, stressing the importance of methods for generation of specific anti-ligands for these potential target ligands.

Many of these differentially expressed molecules are expected to be present on cell surfaces and thereby constitute potential targets for targeted therapies using, e.g., specific antibodies which may be conjugated to bioactive (e.g. cytotoxic) agents.

Large and highly diversified anti-ligand display libraries provide methods of isolating anti-ligands with specificity to unknown cellular ligands of carbohydrate, protein, lipid, or combined actions thereof.

Biopanning processes currently available include whole-cell, cell-portion, and cell membrane based methods that, in principle, permit isolation of display constructs exhibiting anti-ligands specific to cell membrane ligands in their native configuration.

Human and humanized therapeutic antibodies are increasingly used to treat diverse diseases including acute and chronic inflammatory disorders, immunological and central nervous system disorders and cancer. Human therapeutic antibodies are considered the most attractive modalities to treat human disease owing to their fully human nature and associated lack of immunogenicity, optimal ability to engage antibody Fc-dependent host immune effector mechanisms, and their superior in vivo half-life compared to their murine, chimeric and humanized counterparts. Human antibodies are today routinely generated by different technologies including humanized mice and highly diversified phage antibody libraries.

Large ($>10^5$ unique antibody clones) human antibody libraries are sufficiently diversified to contain high affinity antibodies specific for a significant number of antigens including virtually all kinds of auto-antigens. Auto-antigens are antigens that despite being a normal tissue constituent are the target of a humoral or cell-mediated immune response, as in an autoimmune disease and represent an antigen category of outstanding therapeutic interest.

Human antibody libraries are further believed to provide advantages compared to transgenic mice carrying human immunoglobulin genes when selecting for antibodies that bind to receptor epitopes that are structurally conserved between man and mouse, since this category of antibodies is negatively selected for in vivo by mechanisms of self-tolerance. Such conserved regions are of particular therapeutic interest since conserved regions often are functionally-associated (e.g. ligand-binding domains necessary for binding and conferral of ligand/receptor induced cellular responses), and antibodies targeting such conserved epitopes may be screened for in vivo therapeutic activity in syngeneic experimental disease model systems.

High affinity antibodies specific for virtually all kinds of human soluble antigens (e.g. cytokines, chemokines, growth factors, lipids, carbohydrates and conjugate molecules etc), as well as cell surface receptors (e.g. 1TM, 4TM, 7TM and multi-TM spanning receptors, etc) have successfully been isolated from highly diversified human antibody libraries.

Cell surface receptors constitute one category of targets of outstanding therapeutic interest, and several antibodies that bind to different cancer cell associated receptors have been approved for cancer therapy including rituximab (anti-CD20), trastuzumab (anti-Her2), and cetuximab (anti-EGFR).

Therapeutic efficacy is, however, not easily predicted from antibody receptor specificity; antibodies to the same target receptor may vary greatly in therapeutic efficacy independent of their binding affinity (Beers et al., 2008; Cragg and Glennie, 2004) and antibodies against alternative molecular targets may show promising, and sometimes unexpected, therapeutic potential (Beck et al., 2010; Cheson and Leonard, 2008). For example, different CD20 specific antibody clones that bound with similar affinity to the CD20 antigen and carried identical mouse IgG2a constant regions, differ fundamentally in ability to deplete B cells in vivo (Beers et al., 2008; Cragg and Glennie, 2004) and antibodies against other tumor-associated cell surface receptors than CD20 can have significant antitumor activity against B cell cancers (for a review see (Cheson and Leonard, 2008)).

Thus, in a highly diversified antibody library, the most therapeutically efficacious, potent, and best-tolerated antibodies with respect to any given type of cancer are likely to be specific for either of several different receptors, and identifying the therapeutically optimal antibody clones in a highly diversified library requires functional screening of multiple, and ideally all, library members that are specific for different diseased cell-associated receptors.

The applicant has previously developed screening technology (a biopanning method) enabling the retrieval of antibody clones that bind to different surface receptors that are differentially expressed on one cell population (target cells) compared to another (non-target cells) from human phage antibody libraries (WO2004/023140, Fransson et al., 2006; Frendéus, 2006) (hereinafter known as differential biopanning). The disclosure of WO2004/023140 (and all national filings deriving therefrom) is incorporated by reference herein in its entirety.

This screening process consisted of essentially six steps as outlined in FIG. 1. Importantly, this process comprised screening steps in the following order:

1) differential biopanning, followed by
2) screening for target vs non-target specificity, followed by
3) conventional sequencing by Sanger technology of a smaller number of clones.

Using this technology it was possible to generate a pool of antibodies that showed high specificity for target cell versus non-target cell differentially expressed surface receptors.

Sanger sequencing is an example of a technique that is currently used to identify unique binders in a "low throughput" manner. Other examples include running antibody gene DNA on gels before and after restriction enzyme digestion to reveal unique sizes and through different sensitivity to different restriction enzymes, indirectly, different sequences.

When applied to isolating antibodies targeting Cancer B cell (target) versus T cell (non-target) differentially expressed surface receptors ("BnonT" differential biopanning), this process identified antibodies specific for different target cell differentially expressed surface receptors including HLA-DR, surface Ig, and ICAM-1 (Table 1).

TABLE 1

Frequencies and specificities of antibodies isolated by existing screening methodology, e.g. sequential differential biopanning, screen for binding, and Sanger sequencing, targeting Cancer B cell versus T cell differentially expressed surface receptors ("BnonT" differential biopanning)

| Antibody sequence | No of clones (out of 81 tested) | Specificity |
| --- | --- | --- |
| #1 | 71 | sIgM |
| #2 | 4 | HLA-DR |
| #3 | 1 | ICAM-1 |
| #4 | 1 | sIgM |
| #5 | 1 | sIgM |
| #6 | 1 | sIgM |
| #7 | 1 | sIgM |
| #8 | 1 | not determined |

However, targeted receptors were all relatively highly expressed (50,000-400,000 receptors per cell), and the number of unique antibody sequences identified (8 out of 81 screened) by this process was limited.

While only a limited number of clones specific for target cell differentially expressed surface receptors were sequenced, the high frequency of one antibody clone indicated limited antibody diversity in the retrieved "BnonT" antibody pool. Thus, while the technology provided a significant improvement compared to previous cell based panning technologies in the sense that antibodies with therapeutic potential to several different differentially expressed receptors were identified by limited screening effort (Fransson et al., 2006), this observation showed that further improvements were required because, in accordance with the prevailing common view, the panning had only generated an antibody pool of limited diversity and consisting of antibodies against relatively highly expressed and strongly differentially expressed surface receptors (Hoogenboom, 2002) (Liu et al., 2004; Mutuberria et al., 1999; Osbourn et al., 1998).

In silico calculations performed as taught in the earlier biopanning method (WO2004/023140 and Frendéus, 2006) indicated, that the differentially selected "BnonT" antibody pool should contain a much greater number of antibodies against each of several differentially expressed surface receptors (FIG. 2).

The sequencing capabilities at that time made sequencing of a significantly greater number of antibody clones in the pool extremely difficult (practically infeasible), therefore the hypothesis that the differentially selected antibody pool should be much more diversified than apparent by the initial screenings was tested using an indirect approach. Thus, using immunobeads conjugated with recombinant ICAM-1 protein (ICAM-1 being a cell surface receptor targeted by a single antibody clone out of the initially 81 sequenced clones in the differentially selected antibody pool of Table 1), the differentially selected "BnonT" antibody pool was panned for the presence of additional ICAM-1 specific antibody clones. Screening of 1260 antibody clones, retrieved following panning of the differentially selected antibody pool against recombinant ICAM-1, identified twenty-one (21) additional ICAM-1 specific antibody sequences/clones.

These observations demonstrated that the original differential biopanning method could identify antibody clones to differentially expressed antigens but that the differentially selected antibody pool was much more diversified than was apparent from these initial screenings, and significantly more so than as determined by conventional screening approaches The applicant has now devised a way of improving the accuracy of the differential biopanning method for detecting a plurality of different anti-ligands to a ligand of interest. The present invention thus describes methodology enabling the retrieval of a pool of high affinity anti-ligands such as human antibodies that are specific for different ligands (e.g. receptors) differentially expressed in their native cell surface configuration at low to high levels in a target cell population compared to another cell population(s), from human antibody libraries (and other molecular libraries).

Figure 8:
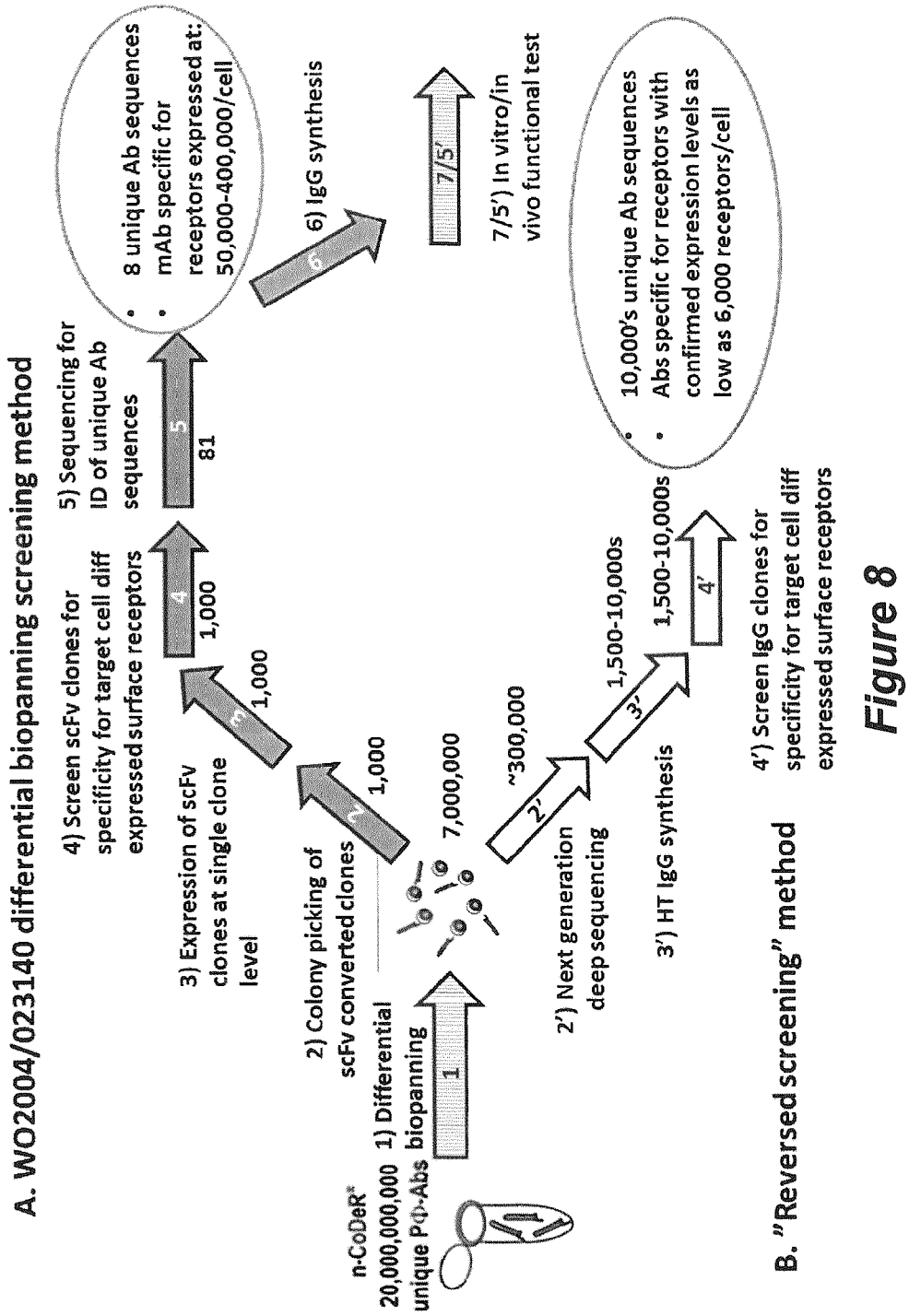

The present invention differs from previously devised screening methodologies in several respects (FIG. 8). Firstly, by combining uniquely powerful differential biopanning methodology with next generation deep sequencing and subsequent confirmatory screening for antibody specificity for target cell differentially expressed surface receptors— "reverse screening", the invention enables generation of an antibody pool that is 1) qualitatively and 2) quantitatively unique.

Importantly, anti-ligands, such as antibody clones, identified by this approach may all have therapeutic potential because based on firstly, their high affinity binding to receptors that are a) differentially expressed on target cells versus non-target cells and b) expressed in their native cell surface configuration on target cells and secondly the documented ability of antibodies with these properties to mediate therapeutic effects in relevant in vitro and in vivo experimental disease model systems (Beck et al., 2010; Fransson et al., 2006).

In summary, therefore, the present invention enables:
1. Generation of an antibody pool by differential biopanning to contain antibodies specific for differentially expressed surface receptors expressed at high, intermediary and low levels
2. A lower threshold for the number of sequenced antibody clones, which must be exceeded in order to identify antibodies specific for intermediary and low expressed surface receptors, exists
3. Above this lower threshold, sequencing of an increasing number of antibody clones increases the number of identified antibodies specific for intermediary and low expressed surface receptors.
4. Comprehensive identification of antibodies specific for intermediary and lower expressed surface receptors in the differentially expressed antibody pool requires deep sequencing.

Therefore, in a first aspect of the invention there is provided a method of isolating at least one anti-ligand to at least one differentially-expressed target ligand comprising the steps of:
(a) performing differential biopanning on a library of anti-ligands so as to isolate at least on anti-ligand; and
(b) performing high throughput sequencing on anti-ligands isolated during step (a).

The method may further comprise the step of:
(c) performing confirmatory screening for antibody specificity for the differentially-expressed ligand The differential biopanning step of the method of the invention may comprise the sub-steps of:
(i) providing a library of anti-ligands;
(ii) providing a first population of ligands comprising a ligand fixed to or incorporated in a subtractor ligand construct;
(iii) providing a second population of ligands comprising the same ligand as step (ii), fixed to or incorporated in a target ligand construct;
(iv) determining an amount of the subtractor ligand construct and the target ligand construct in the populations using one or more equations derived from the universal law of mass action $$\frac{[C]^c[d]^d}{[A]^a[B]^b} = K_{eq},$$

where:
A, B, C & D=are the participants in the reaction (reactants and products)
a, b, c, & d=the coefficients necessary for a balanced chemical equation
so as to permit isolation of anti-ligand to differentially expressed target ligand;
(v) providing the amount of subtractor ligand construct as determined in step (iv);
(vi) providing the amount of target ligand construct as determined in step (iv);
(vii) providing separation means for isolating anti-ligand bound to the target ligand construct from anti-ligand bound to a subtractor ligand construct;
(viii) exposing the library of (i) to the ligand constructs provided by (v) and (vi) to permit binding of anti-ligands to ligands; and (ix) using the separation means to isolate anti-ligand bound to the ligand fixed to or incorporated in the target ligand construct.

It is not intended that the steps of the invention necessarily have to be performed in any specific order.

By "providing the determined amount" we include the meaning of providing an amount of ligand that was already known such that the equations of the invention have been used to verify that the known amount provided is suitable for isolating the desired anti-ligand(s).

The reaction parameters that are utilised for a given selection process may be optimised according to the present invention by calculations applying the Mass Law of Action and equations derived therefrom, and taking parameters such as molecular library diversity, anti-ligand copy number, desired detection limit of upregulation, desired anti-ligand affinity, and ligand concentration into consideration.

The high throughput sequencing step of the method of the first aspect may be conducted by 454 sequencing, Illumina, SOLiD methods, the Helicos system or those from Complete Genomics and Pacific Biosciences The advent of next generation sequencing has enabled sequencing of large numbers (1,000s to 1,000,000s) candidate genes in high-throughput manner (from here on referred to as "deep sequencing") 454 sequencing is described (and incorporated by reference herein) by Margulies et al. (2005). In the 454 method, the DNA to be sequenced is either fractionated and supplied with adaptors or segments of DNA can be PCR-amplified using primers containing the adaptors. The adaptors are nucleotide 25-mers required for binding to the DNA Capture Beads and for annealing the emulsion PCR Amplification Primers and the Sequencing Primer. The DNA fragments are made single stranded and are attached to DNA capture beads in a manner that allows only one DNA fragment to be attached to one bead. Next, the DNA containing beads are emulsified in a water-in-oil mixture resulting in microreactors containing just one bead.

Within the microreactor, the fragment is PCR-amplified, resulting in a copy number of several million per bead. After PCR, the emulsion is broken and the beads are loaded onto a pica titer plate. Each well of the pico-titer plate can contain only one bead. Sequencing enzymes are added to the wells and nucleotides are flowed across the wells in a fixed order. The incorporation of a nucleotide results in the release of a pyrophosphate, which catalyzes a reaction leading to a chemiluminescent signal. This signal is recorded by a CCD camera and a software is used to translate the signals into a DNA sequence.

In the Illumina method (Bentley (2008)), single stranded, adaptor-supplied fragments are attached to an optically transparent surface and subjected to "bridge amplification". This procedure results in several million clusters, each containing copies of a unique DNA fragment. DNA polymerase, primers and four labeled reversible terminator nucleotides are added and the surface is imaged by laser fluorescence to determine the location and nature of the labels. Protecting groups are then removed and the process is repeated for several cycles.

The SOLID process (Shendure (2005)) is similar to 454 sequencing, DNA fragments are amplified on the surface of beads. Sequencing involves cycles of ligation and detection of labeled probes.

Several other techniques for high-throughput sequencing are currently being developed. Examples of such are The Helicos system (Harris (2008)), Complete Genomics (Drmanac (2010)) and Pacific Biosciences (Lundquist (2008)). As this is an extremely rapidly developing technical field, the applicability to the present invention of high throughput sequencing methods will be obvious to a person skilled in the art While instruments capable of sequencing long stretches of DNA, such as those coding for antibody variable domains (Fv), scFv or Fab sequences are only at prototypical stage, currently available instruments do enable sequencing of shorter stretches of DNA such as sequences coding for, and spanning, scFv CDRH1 to CDRH3 domains. However, as the sequencing technology improves to allow long stretch DNA sequencing, these techniques will also work well within the methods of the invention.

The confirmatory screening step of the method of the invention may be conducted by detecting specific ligand binding of the isolated anti-ligand pool and/or individual anti-ligand clones to a target construct vs. a subtractor construct using any assay addressing ligand/anti-ligand binding, e.g. Flow-cytometry, FMAT (Fluorescent Microvolumetric Assay Technology), ELISA (Enzyme-linked immunosorbent assay), MSD (Meso Scale Discovery) and CBA (Cytometric Bead Array).

In one embodiment the ligand of the method is not expressed on one of either the target construct or the subtractor construct, i.e. it is only expressed on one of the target construct or the subtractor construct.

In another embodiment the ligand of the method is expressed at higher levels on one of either the target construct or the subtractor construct.

The differential biopanning method can comprise the further sub-step of releasing the anti-ligand from the ligand.

Preferably, steps (ii) to (ix) of the differential biopanning step are conducted in parallel to isolate a plurality of anti-ligands to a plurality of different ligands.

Steps (ii) to (ix) of the differential biopanning step are repeated one or more times.

Preferably, the amount in the differential biopanning step of one of the subtractor construct or target construct is provided in excess of the amount of the other of the subtractor construct or target construct. The excess of ligand can be between 10 and 1000 fold, but can also be between 2 and 10 fold, or 1000 and 100,000 fold.

The magnitude of excess of subtractor ligand population determines the highest possible "resolution" (i.e. how well you are able to discriminate between anti-ligands with specificity for ligands that are low upregulated, moderately upregulated, highly upregulated, or uniquely expressed) that you will be able to detect, and how well you will be able to discriminate between differently expressed ligands. For example, if you are using a library with 100 target ligand specific anti-ligands and you add large enough concentrations of positive ligand so that all anti-ligand will be bound to ligand at equilibrium, then a subtractor ligand population excess of 10-fold will allow you to reduce the frequency of anti-ligands with specificity for commonly expressed ligands by 90%, whereas a 200-fold excess (twice the number of anti-ligand specific binders) would allow you to remove common binders (see WO 2004/023140, FIG. 5 and the very last paragraph of example 4 for data showing this).

In one embodiment the equation of step (iv) of the differential biopanning step is:

$$bA = \frac{(A + T + (K_d) \times (C \times V))}{2} - \sqrt{\frac{(A + T + (K_d) \times (C \times V))^2}{4} - A \times T}$$

where
- $bA$ = Bound anti-ligand
- $A$ = Total number of anti-ligand
- $T$ = Total number of ligands
- $C$ = Avogadro's constant (6.022×10²³ particles/mole)
- $V$ = Reaction volume (liters)
- $K_d$ = Equilibrium dissociation constant And in an alternative embodiment the equation in step (iv) of the differential biopanning step is:

$$bA = \left\{\frac{(A+T+(K_d)\times(C\times V))}{2} - \sqrt{\frac{(A+T+(K_d)\times(C\times V))^2}{4} - A\times T}\right\} \times \left\{\frac{(T_p \times C_p)}{((T_p \times C_p)+(T_s \times C_s))}\right\}$$

where
- $bA_p$ = Bound anti-ligand
- $T_p$ = The number of ligands on $C_p$
- $T_s$ = The number of ligands on $C_s$
- $C_p$ = The number of target ligand constructs
- $C_s$ = The number of subtractor ligand constructs
- $A$ = Total number of anti-ligand
- $T$ = Total number of ligands
- $C$ = Avogadro's constant (6.022×10²³ particles/mole)
- $V$ = Reaction volume (liters)
- $K_d$ = Equilibrium dissociation constant The separation means of the differential biopanning step may be selected from at least one of a solid support, cell membrane and/or portions thereof, synthetic membrane, beads, chemical tags and free ligand. The separation means of the subtractor and target constructs may have a different density. The separation means of the subtractor construct can preferably be a membrane vesicle or a whole cell membrane.

Step (ix) of the differential biopanning method may be performed by at least one of the method of separation is one of density centrifugation (Williams and Sharon, 2002), solid support sequestration, magnetic bead sequestration (Siegel et al., 1997), chemical tag binding and aqueous phase partitioning.

More preferably the method of separation is density centrifugation performed on a density gradient e.g. Ficoll; Percoll; iodinated gradient media, wherein during centrifugation, the first and second target ligands move through the Ficoll gradient to differing extents whereby the first and second target ligands can be isolated from their differing end points.

Most preferably the method of separation uses a sucrose-polymer gradient e.g. Ficoll.

The library of step (a) is preferably a display library comprising a plurality of library members which display anti-ligands. An example of such a library is a phage display library wherein the anti-ligand is displayed on the surface of a bacteriophage.

The display of proteins and polypeptides on the surface of bacteriophage (phage), fused to one of the phage coat proteins, provides a powerful tool for the selection of specific ligands. This 'phage display' technique was originally used by Smith in 1985 to create large libraries of antibodies for the purpose of selecting those with high affinity for a particular antigen. More recently, the method has been employed to present peptides, domains of proteins and intact proteins at the surface of phage in order to identify ligands having desired properties.

The principles behind phage display technology are as follows:

(i) Nucleic acid encoding the protein or polypeptide for display is cloned into a phage;

(ii) The cloned nucleic acid is expressed fused to the coat-anchoring part of one of the phage coat proteins (typically the p3 or p8 coat proteins in the case of filamentous phage), such that the foreign protein or polypeptide is displayed on the surface of the phage;

(iii) The phage displaying the protein or polypeptide with the desired properties is then selected (e.g. by affinity chromatography) thereby providing a genotype (linked to a phenotype) that can be sequenced, multiplied and transferred to other expression systems.

Alternatively, the foreign protein or polypeptide may be expressed using a phagemid vector (i.e. a vector comprising origins of replication derived from a phage and a plasmid) that can be packaged as a single stranded nucleic acid in a bacteriophage coat. When phagemid vectors are employed, a "helper phage" is used to supply the functions of replication and packaging of the phagemid nucleic acid. The resulting phage will express both the wild type coat protein (encoded by the helper phage) and the modified coat protein (encoded by the phagemid), whereas only the modified coat protein is expressed when a phage vector is used.

The use of phage display to isolate ligands that bind biologically relevant molecules has been reviewed in Felici et al., (1995), Katz (1997) and Hoogenboom et al. (1998). Several randomised combinatorial peptide libraries have been constructed to select for polypeptides that bind different targets, e.g. cell surface receptors or DNA (Kay and Paul, (1996)).

Proteins and multimeric proteins have been successfully phage-displayed as functional molecules (see Chiswell and McCafferty, (1992)). In addition, functional antibody fragments (e.g. Fab, single chain Fv [scFv]) have been expressed (McCafferty et al. (1990); Barbas et al. (1991); Clackson et al. (1991)), and some of the shortcomings of human monoclonal antibody technology have been superseded since human high affinity antibody fragments have been isolated (Marks et al. (1991) and Hoogenboom and Winter (1992)).

Further information on the principles and practice of phage display is provided in *Phage display of peptides and proteins: a laboratory manual* Ed Kay, Winter and McCafferty (1996), the disclosure of which is incorporated herein by reference.

The anti-ligand library can be constructed from at least one selected from antibodies, and antigen binding variants, derivatives or fragments thereof; scaffold molecules with engineered variable surfaces; receptors; and enzymes.

The differentially expressed ligand may be at least one selected from antigens; receptor ligands; and enzyme targets that comprise at least one from carbohydrate; protein; peptide; lipid; polynucleotide; inorganic molecules and conjugated molecules.

The method of the invention may also comprise a further step of exposing the ligand and its separation means (from the differential biopanning steps) to a stimulus which influences the expression of target ligands on said ligand constructs.

Selected anti-ligands identified by the invention may subsequently be used in the manufacture of a pharmaceutical composition for use in medicine for the treatment, imaging, diagnosis or prognosis of disease. Anti-ligands based on antibodies and most importantly on human antibodies have great therapeutic potential.

Therefore, in a second aspect of the invention there is provided a method for preparing a pharmaceutical composition which comprises, following the identification of an anti-ligand with desired characteristics by a method according to any preceding claim, adding said anti-ligand to a pharmaceutically acceptable carrier.

In a third aspect of the invention there is provided a pharmaceutical composition prepared by the method of the second aspect for use in medicine. The pharmaceutical composition may also be used in the manufacture of a medicament for the prevention, treatment, imaging, diagnosis or prognosis of disease.

Definitions

By "biopanning" we mean a method of selection of one member from a desired anti-ligand—ligand-binding pair, based on its ability to bind with high affinity to the other member.

By "differential biopanning" we mean a biopanning method to select one member from a desired anti-ligand—ligand-binding pair that is expressed in different amounts in or on two different sources (e.g. a subtractor/control and target), based on its ability to bind with high affinity to the other member By "high throughput sequencing" we include the meaning that a large number of sequences are sequenced in parallel (up to millions) such that the speed of sequencing large numbers of molecules is practically feasible and made significantly quicker and cheaper.

By "confirmatory screening" we mean detecting specific ligand binding of the isolated anti-ligand pool and/or individual anti-ligand clones to a target construct vs. a subtractor construct using any assay addressing ligand/anti-ligand binding, e.g. Flow-cytometry, FMAT, ELISA, MSD and CBA. The term further includes the meaning that once an anti-ligand is identified as binding to a differentially expressed ligand, the nature and identity of the ligand and the binding interactions between anti-ligand and ligand are studied By "ligand" we include the meaning of one member of a ligand/anti-ligand binding pair. The ligand may be, for example, one of the nucleic acid strands in a complementary, hybridised nucleic acid duplex binding pair; an effector molecule in an effector/receptor binding pair; or an antigen in an antigen/antibody or antigen/antibody fragment binding pair.

By "anti-ligand" we include the meaning of the opposite member of a ligand/anti-ligand binding pair. The anti-ligand may be the other of the nucleic acid strands in a complementary, hybridised nucleic acid duplex binding pair; the receptor molecule in an effector/receptor binding pair; or an antibody or antibody fragment molecule in antigen/antibody or antigen/antibody fragment binding pair, respectively.

By "antigen" we include the meaning a molecule or chemical compound that is able to interact with antibodies but not necessarily produce an immune response. Such antigens include, but are not limited to molecules of protein, peptide, nucleotide, carbohydrate, lipid or a conjugate thereof.

By "differentially expressed ligands" we mean ligands that are either expressed at differing levels between the target and subtractor sources, including those expressed only in certain conditions/places and not in others; or where either the target or subtractor ligand is a modified version of the other from the target and subtractor ligands. For example, some antigens are highly expressed on the cell surfaces of diseased cells (e.g. cancer cells) and at low levels or not at all on the equivalent healthy cells (e.g. non-cancerous cells).

By "low expression ligands" we mean those ligands that are expressed at low levels i.e. less than 20,000 copies per cell, e.g. between 5,000 and 20,000 (this includes most wild-type expressed cell surface receptors) or ligands occurring at a frequency of less than 1% of any other, more highly expressed ligand in the positive ligand population sample.

By "ligand construct" we mean a system which comprises target and/or subtractor ligand associated with separation means.

The term "antibody variant" shall be taken to refer to any synthetic antibodies, recombinant antibodies or antibody hybrids, such as, but not limited to, a single-chain antibody molecule produced by phage-display of immunoglobulin light and/or heavy chain variable and/or constant regions, or other immunointeractive molecule capable of binding to an antigen in an immunoassay format that is known to those skilled in the art.

The term "antibody derivative" refers to any modified antibody molecule that is capable of binding to an antigen in an immunoassay format that is known to those skilled in the art, such as a fragment of an antibody (e.g. Fab or Fv fragment), or an antibody molecule that is modified by the addition of one or more amino acids or other molecules to facilitate coupling the antibodies to another peptide or polypeptide, to a large carrier protein or to a solid support (e.g. the amino acids tyrosine, lysine, glutamic acid, aspartic acid, cysteine and derivatives thereof, $NH_2$-acetyl groups or COOH-terminal amido groups, amongst others).

By "density centrifugation" we mean the separation of items, e.g. cells, organelles and macromolecules, according to their density differences. This separation is achieved by centrifugation using a density gradient of an appropriate solution, through which the items being separated move on the basis of their density.

The "Law of Mass Action" is a universal law of nature that is applicable under any circumstance. This law states that for the reaction:

$$aA+bB \rightarrow cC+dD$$

and if that system is at equilibrium at a given temperature, then the following ratio is a constant:

$$\frac{[C]^c[d]^d}{[A]^a[B]^b} = K_{eq}$$

where:
A, B, C & D=are the participants in the reaction (reactants and products)
a, b, c, & d=the coefficients necessary for a balanced chemical equation
And wherein the constant is calculated in terms of concentration (indicated by [ ]) and K has units $M^{c+d-(a+b)}$.

Examples embodying certain aspects of the invention shall now be described, with reference to the following figures in which:—

FIG. 1—Schematic of the differential biopanning method described in (Fransson et al Int J Canc 2006). Numbers below arrows indicate the number of phage-abs or antibody clones that are retained in the screening process following each of the five screening steps (1 to 5) and two subsequent synthesis and verification steps (6) and (7). The steps are: (1) Differential biopanning, (2) Colony picking of scFv converted clones, (3) expression of scFv clones at single clone level, (4) Screen scFv clones for specificity for target cell diff expressed surface receptors, (5) Sequencing for ID of unique Ab sequences, (6) IgG synthesis, and (7) in vitro/in vivo functional test FIG. 2—In silico calculations showing that the antibody pool derived from differential biopanning of Cancer B cells versus Jurkat T cells ("BnonT") should contain a much greater number of antibodies against each of several differentially expressed surface receptors than experimentally is identified using conventional methods (1) indicates Calculations were performed as taught in WO2004/023140

FIG. 3. The phage-antibody pool derived from differential biopanning of DU-145 prostate cancer versus Jurkat T cells ("DnonT") is highly specific for the target cell (DU-145) population.

A) Graph shows the dose-dependent specific binding of the phage-pool, obtained following two rounds of differential biopanning, to the target DU145 cells as analyzed by FACS. Note that there is no detectable binding to non-target Jurkat cells.

B) The graph shows the specific binding of each of 1408 individual, randomly selected, clones from the pool obtained after two rounds of differential biopanning of DU145 cells versus Jurkat cells as analyzed by FMAT.

FIG. 4. Target DU-145 cells express several surface receptors that can be classified as "highly differentially expressed", "intermediary differentially expressed", or "lowly differentially expressed" based on their absolute target cell expression level and their relative expression level on target versus non-target cell surfaces.

Target (DU145) and non-target (Jurkat) cells were screened for expression of three antigens; HER2, CD24 and CD130 by Flow Cytometry using Zenon Alexa Fluor 647 labelled antibodies.

A) Figure shows the mean fluorescence intensity of target and non-target cells stained with zenon labelled antibodies.

B) Figure shows the percentage of cells that express HER2, CD24 and CD130.

FIG. 5. Scatchard plot analyses reveals that expression levels of differentially expressed surface receptors targeted by antibodies isolated by differential biopanning and deep sequencing range from 6,000-400,000 receptors per cell.

A. Saturation curves

B. Rosenthal plots. The affinity (KD) of the anti-CD130 antibody was estimated to be 0.8 nM and the number of CD130 surface receptors 6.300/cell. Affinity of the anti-CD24 antibody was estimated to be 5.6 nM and the number of epitopes 8.400/cell. The affinity of anti-HER2 was estimated to be 47 nM and the number of epitopes to 110,000/cell. Evaluation was done with Rosenthal plots of the $^{125}$I labelled antibodies binding to INF gamma stimulated DU145 cells.

Figure 6:
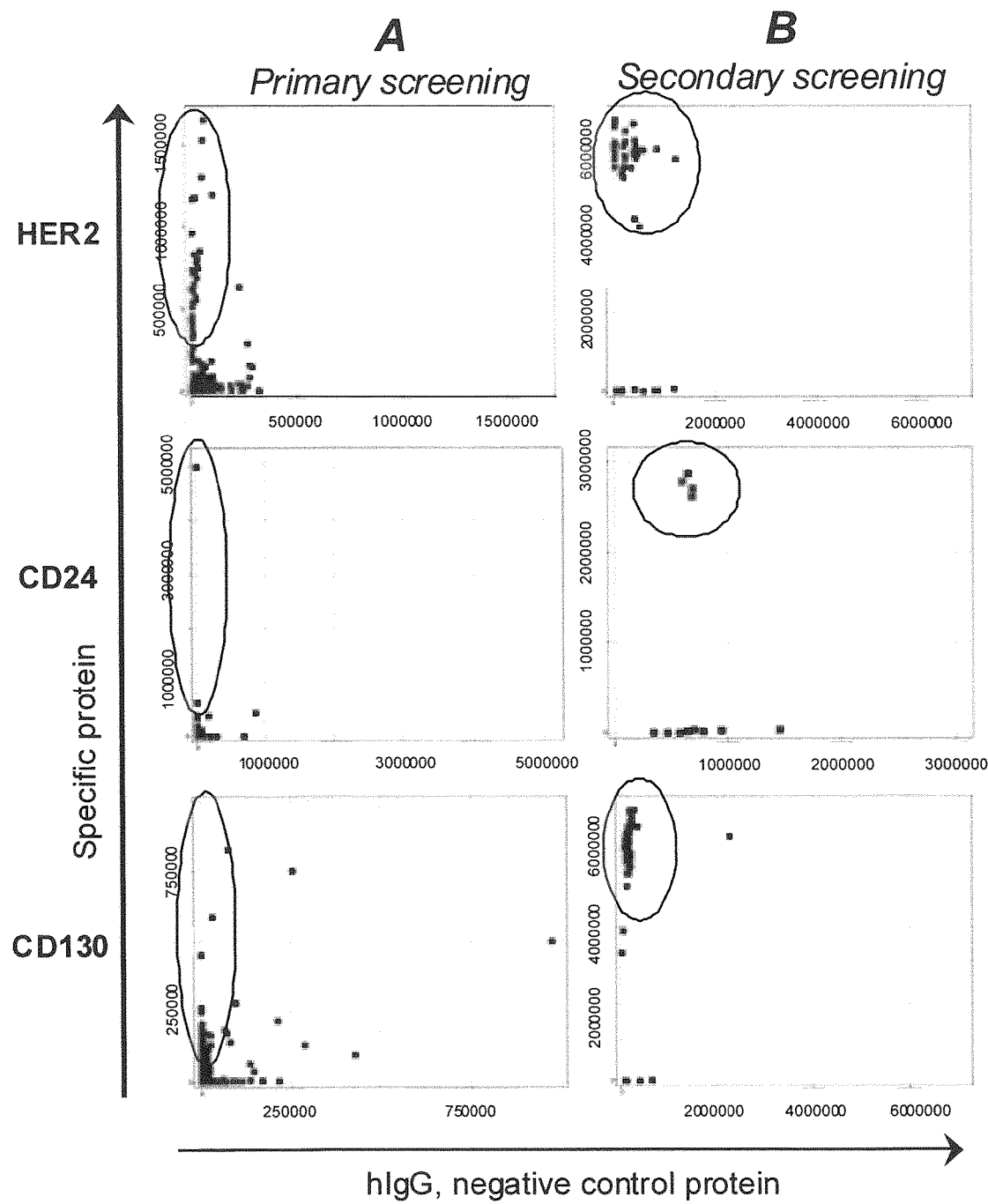

FIG. 6. The antibody pool derived from differential biopanning of DU-145 prostate cancer versus Jurkat T cells ("DnonT") contains antibody clones specific for highly expressed, intermediary expressed, and low expressed differentially expressed surface receptors.

Based on scatchard and FACS analyzes (FIGS. 4 and 5), HER2, CD24, and CD130 were characterised as receptors being expressed at varying levels.

A) The figure shows that antibody clones specific for all antigens are present in the antibody pool generated by two rounds of differential biopanning of DU-145 vs Jurkat cells as analyzed by ELISA.

B) The figure shows that when target specific clones in A were selected and re-tested for binding, the majority of the clones were still positive for the target antigen.

Sequencing of retrieved target surface receptor specific antibody clones demonstrated the presence of (at least) 12 unique antibodies in the differentially selected antibody pool; eight (8) anti-HER2, one (1) anti-CD24 and three (3) anti-CD130 antibodies.

Figure 7:
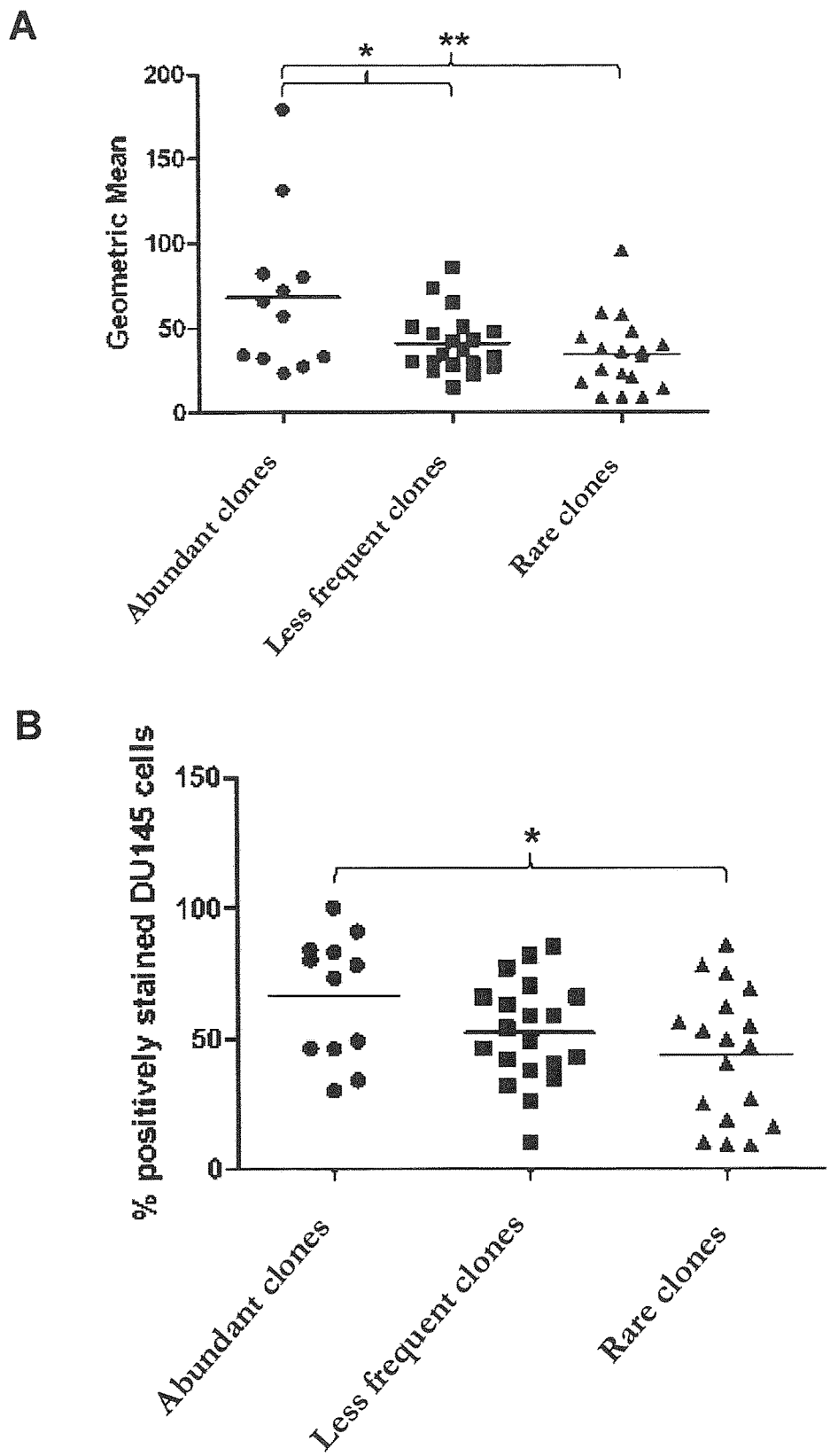

FIG. 7. Sequencing of an increasing number of differentially selected antibody clones results in identification of an increasing number of antibody clones specific for low expressed target cell differentially expressed surface receptors.

Antibody clone sequences in three randomly selected pools of binders of increasing size (91 clones, 255 clones, and 813 clones, respectively) were determined. Thereafter, clones that were found in all three pools ("abundant clones)", found only in the two larger pools ("less frequent clones"), or only in the largest pool ("rare clones") were analyzed for binding to DU145 cells by FACS and mean fluorescence intensities of abundant, less frequent and rare clones were compared.

The data clearly demonstrate that mean receptor expression levels for abundant clones>intermediary frequent clones>rare clones. Thus, sequencing of an increasing number of differentially selected antibody clones resulted in identification of an increasing number of antibody clones specific for low expressed target cell differentially expressed surface receptors A) Figure shows the mean fluorescence intensity of DU-145 cells stained with the respective antibody clones.

B) Figure shows the percentage of target cells that the individual antibody clones bind to.

Since the clones were randomly selected, some of them were non-binders and these were taken away before analysis (a binder was defined either as a clone giving a signal at least twice the negative control on both percent positively stained cells and the geometric mean, or alternatively, three times as high signal in geometric mean).

*=p<0.05, **=p<0.01 as calculated by ANOVA using Bonferroni's correction for multiple analyzes.

FIG. 8—The schematic depicts a comparison of the screening steps of the previously described differential biopanning screening method (A., upper panel) and the new enhanced method (B., lower panel).

The two methods differ in several respects; Firstly, in the reversed screening method Phage-ab to scFv conversion, scFv expression, and scFv screen for binding specificity steps of the WO2004/023140 differential biopanning have been omitted. Second, in the reversed screening method differential biopanning is followed directly by (deep) sequencing whereas in the WO2004/023140 screening process sequencing of antibody clones in the pool is preceded by screening of individual scFv clones for target cell differentially expressed surface receptor specificity. Third, and most importantly, the number of antibody clones (10,000's) and quality of antibody clones (including comprehensive generation of antibodies specific for low expressed differentially expressed receptors) achieved using the reversed screening process can practically not be achieved using the previously described differential biopanning method of A.

The steps are: (1) Differential biopanning, (2) Colony picking of scFv converted clones, (3) Expression of scFv clones at single clone level, (4) Screen scFv clones for specificity for target cell diff expressed surface receptors, (5) Sequencing for ID of unique Ab sequences, (6) IgG synthesis, (7) In vitro/in vivo functional test, (2') Next generation deep sequencing, (3') HT IgG synthesis, (4') Screen IgG clones for specificity for target cell diff expressed surface receptors, (5') In vitro/in vivo functional test FIG. 9—In silico calculations of retrieved phage-antibody pool derived from two rounds of differential biopanning of DU-145 prostate cancer versus Jurkat T cells.

EXAMPLE 1—COMBINING DIFFERENTIAL BIOPANNING WITH SUBSEQUENT HIGH-THROUGHPUT SEQUENCING GENERATES AN UNPRECEDENTED NUMBER OF UNIQUE ANTIBODY CLONES SPECIFIC FOR DIFFERENTIALLY EXPRESSED TARGET CELL SURFACE RECEPTORS

Generation of an Antibody Pool by Differential Biopanning of Cancer B Cells Versus Jurkat T Cells ("BnonT")

In this experiment $2 \times 10^{13}$ phage particles from the highly diversified n-CoDeR library comprising some $10^{10}$ genotype unique binders are mixed with whole B lymphoma cell line Ramos cells (positive selection), and plasma membrane or crude membrane vesicles from the T leukaemia cell line Jurkat (negative selection). Binders specific for antigens that are uniquely expressed on the B lymphoma cell line Ramos, compared to the T cell leukaemia cell line Jurkat, are to be selectively isolated.

Positive and Negative Cell Number Calculation for Selection

Cell numbers to be used in the different selections round were calculated as taught in (WO 2004/023140). Reaction parameters used for calculations were as shown in FIG. 2

Positive and negative cell numbers were chosen such that, following three rounds of selection, binders with specificity for antigens expressed uniquely on B cells will be enriched 10,000-fold over an antigen expressed at equal density on B and T cells.

The input number of phage binders specific for different categories of antigen (positive cell enriched, positive cell unique, or positive/negative cell commonly expressed antigen) in selection rounds 2 and 3 was calculated by multiplying the calculated number of eluted phage, specific for different categories of antigen following selection rounds 1 and 2, with the amplification factor (AF).

The amplification factor was obtained by dividing total number of amplified phage following the relevant selection round with the total number of eluted phage from the same selection round.

Experimental Methods

Cell Cultures

The Jurkat T cell line, clone E6-1, and the Ramos B lymphoma cell line, were cultured in RPMI 1640 supplemented with 10% FCS (heat-inactivated for Ramos Cells only), 10 mM HEPES and 1 mM Sodium pyruvate, in a humidified atmosphere at 37° C. The cells were maintained at $1-2 \times 10^6$ cells/ml (<$1 \times 10^6$ cells/ml for Jurkat).

Jurkat T Cell Plasma Membrane Preparation

Jurkat Cell Culture

Jurkat E6-1 cells were maintained in RPMI-1640 with Glutamax I (Gibco, #61870-010) supplemented with 10% foetal calf serum (Gibco, Lot no 1128016) 1 mM Sodium pyruvate (Gibco) and 10 mM Hepes buffer (Gibco) in a humidified atmosphere of 5% $CO_2$ at 37° C., and at cellular densities between $1 \times 10^5$ to $1 \times 10^6$ cells/ml. In the final passage, cells were allowed to reach a maximal density of $2 \times 10^6$, at which point they were harvested.

Cell Disruption

1. Cells were harvested from culture by centrifugation in 500 ml Centrifuge tubes (Corning, #431123) placed in tube adapters, 1500 rpm, 15 min at 4° C.
2. The supernatant was discarded and washed in 0.145M NaCl. Cell suspensions were pooled, cells counted ($5 \times 10^9$ cells total), and centrifugation repeated.
3. Cell disruption was performed by hypo-osmotic shock in 1 mM $NaHCO_3$ 1.5 mM MgAc pH 7.4 on ice for 10-30 min and subsequent nitrogen cavitation occurred in a Veda press, 40 bar (4000 kPa) for 15 min at 0° C. Cell concentration did not exceed $5 \times 10^7$ cells/ml.
4. Following disruption 150 µl 0.5M EDTA was added to the homogenate suspension to yield a final EDTA concentration of 1 mM (addition of EDTA prevents aggregation of membrane vesicles).
5. A) Crude membrane isolation: The homogenate (50 ml) was centrifuged for 10 min at 1900 g (4000 rpm in a SS34 rotor) to remove unbroken cells and nuclei, and the supernatant collected. Washing and re-centrifugation of pellet was avoided, as the fragile nuclei tend to disrupt, causing DNA leakage and aggregation; or
   B) Plasma membrane isolation: 10 ml of 37.2% sucrose was layered at the bottom of 6×38.5 ml Beckman ultra centrifugation tube, and 6×27 ml of the cell homogenate from step 2 above was carefully layered on top. The tube was centrifuged at 27000 rpm in a swing-out SW28 rotor (6×39 ml nominal capacity) for 2 h 45 min at 4° C. Plasma membranes were isolated from the tubes as the white band of the interphase between the sucrose cushion and the sample phase, and PM were pooled, split between 4×35 ml tubes and diluted in TE buffer (1 mM Tris/0.25M sucrose/0.25M EDTA buffer) to a total volume of 35 ml.
6. Ultra-centrifugation was performed in a Beckman Type 45.Ti rotor (nominal capacity 6×94 ml Nalgene tubes) at 40,000 rpm (approx. 200,000×g) for 1 h at 4° C.
7. The supernatants were discarded and any remaining buffer was removed using a 1 ml Finn pipette. The plasma membrane pellets were scraped off the bottom of tubes with a metal bar, and transferred to a small dounce homogeniser. Pelleted membranes were re-suspended by homogenisation in a total volume of 2.5 ml TE-buffer containing 10 mM Hepes (10 mM Hepes/1 mM Tris/0.25M sucrose/0.25M EDTA buffer) by 5-10 strokes with a loose fitting Dounce glass piston. Approximately, membranes derived from some $2 \times 10^9$ Jurkat cells can be resuspended per ml of resuspension (TE) buffer.

Protein Concentration Determination

Protein concentration determination was performed using the BCA kit according to the manufacturer's instructions. Briefly, a double BSA standard was prepared by 2-fold dilutions (10 µl sample+10 µl buffer) in PBS of a 2 mg/ml BSA stock solution. A standard curve was generated and used to determine the total protein concentration of membrane samples.

Plasma Membrane Activity (by Alkaline Phosphatase Assay)

Alkaline Phosphatase Solutions

Substrate Solution:

1 tablet p-NPP per 10 ml borate buffer (1.5 mg/ml final concentration) in 50 mM sodium borate buffer (pH 9.8), 1.0 mM $MgCl_2$ Triplicate samples were diluted in Borate/$MgCl_2$ buffer by transferring 500 µl sample to 50 µl dilution buffer (50 mM sodium borate buffer (pH 9.8), 1.0 mM $MgCl_2$). 200 µl substrate solution (1 tablet p-NPP per 10 ml borate buffer to 1.5 mg/ml final concentration in 50 mM sodium borate buffer, pH 9.8, 1.0 mM MgCl$_2$) was added to two of three samples for each dilution. The samples were then incubated at 37° C. for 60 plus minutes. The absorbance of the supernatant was measured at 410 nm, and the values from appropriate control well(s) (e.g. total Nitrogen cavitated cell homogenate, nuclei and heavy mitochondria excluded) where substrate was not added were subtracted. The results were plotted and analysed.

Selection Procedure: Differential Biopanning Protocol
Reaction Parameters
1$^{st}$ Selection Round n-CoDeR Lib2000 phage stock comprising 10$^{10}$ genotype unique phagemid particles (Amp$^r$) amplified to 2×10$^{13}$ total pfu in 1.6 ml 2% milk-PBS (with Ca and Mg).

Total reaction volume 2.5 ml
Positive—5×10$^7$ Ramos B cell lymphoma cells
Negative—Jurkat T cell crude membranes derived from 2×10$^9$ cells 2$^{nd}$ Selection Round 1.5×10$^{12}$ phage eluted from previous selection round and then amplified, precipitated and re-suspended in 100 µl 2% milk-PBS (with Ca and Mg).

Total reaction volume 0.5 ml
Positive—5×10$^6$ Ramos B cell lymphoma cells
Negative—Jurkat T cell crude membrane vesicles derived from 1×10$^9$ cells 3rd Selection Round 1×10$^{12}$ phage eluted and amplified from previous selection round re-suspended in 100 µl 2% milk-PBS (with Ca and Mg).

Total reaction volume 0.5 ml
Positive—5×10$^6$ Ramos B cell lymphoma cells
Negative—Jurkat T cell plasma membrane vesicles derived from 1×10$^9$ cells Method The phage stock was pre-warmed at 37° C. for 15 min and vortexed intermittently. The phage stock was centrifuged for 15 min at full speed in an eppendorf centrifuge. Where a precipitate had formed, the supernatant was transferred to a new eppendorf tube and resuspended in non-fat milk to a final concentration of 2%.

Control Jurkat cell plasma membrane preparations from 2×10$^9$ cells (1×10$^9$ cells biopanning rounds 2 and 3) were thawed on ice. (10 µl was also saved for protein concentration determination.) The thawed plasma membrane preparations were resuspended by adding phage stock and by mixing with a pipette and subsequently incubated for 15 minutes on ice.

5×10$^7$ (5×10$^6$ cells biopanning rounds 2 and 3) Ramos cells were centrifuged at 1200 rpm, 6 min, 4° C.

The supernatant was discarded and the Ramos cells resuspended in the milk-phage-negative cell membrane stock solution and incubated at 10° C. and subjected to slow (end-over-end) rotation for 4 hours.

The cell/cell membrane/phage incubate was transferred to a 15 ml Falcon tube containing 1 ml 100% (trypan blue stained) Ficoll at the bottom, and 9 ml overlaid 40% Ficoll-Paque Plus in 2% BSA/PBS (with Ca and Mg). The tube was centrifuged at 1500 rpm for 10 min, 4° C., rotated 180° and centrifuged for a further 1 minute in order to dislodge cells from the tube wall.

The interface containing whole Ramos cells and bound phage was carefully aspirated using a syringe and a higher gauge needle (e.g. Microlance 3-19GA11/2 1.1×40 TW PM). The needle was inserted just below the cell-containing interface with the bevelled end of the needle facing up. The cell layer was collected (approximately 150 µl) and the needle pushed through the plastic of the tube opposite to the entrance hole. The contents of the syringe were expelled into a fresh tube, and washed twice by sucking up fresh PBS into the needle (still situated as piercing the tube). The harvested cell suspension was resuspended in 500 µl of PBS-2% BSA and washing repeated, saving the supernatant for titration.

Cells were resuspended in 1 ml PBS and transferred to a new 15 ml Eppendorf tube in which they were centrifuged at 1260 rpm for 10 min, 4° C. The supernatant was removed using a pipette, saving the supernatant for titration.

The phage were eluted from cells by addition of 150 µl of 76 mM citric acid (pH2.5) in PBS followed by incubation at room temperature for 5 min. The mixture was neutralised by addition of 200 µl of 1M Tris-HCl, pH 7.4. The cells were then centrifuged and the eluted phage saved.

The cells were resuspended in 1 ml trypsin and transferred to a new tube and incubated for 10 min before inactivation with 40 µl mg/ml aprotinin. The cells were centrifuged, saving the supernatant for titration.

Amplification on Large Plates Following Selection Rounds 1 and 2

1. 10 ml E. coli HB101F' cultures were started (one for each selection to be amplified+one for OD600 measurement) 2.5-3 h before use by addition of 50 ml overnight culture to 10 ml LB (lysogeny broth) containing 15 µg/ml Tetracycline. OD was checked on one culture after approximately 2.5 h.
2. The tubes were infected with half the eluted phage at OD$_{600}$=0.5.
3. The tubes were incubated for 30 minutes at 37° C. and 50 rpm, and for proper phenotyping an additional 30 min at 37° C., 200 rpm.
4. The bacteria were concentrated (10 ml) by centrifugation for 10 minutes at 2060×g (3000 rpm Beckman GS-6).
5. The bacteria were resuspended in part of the supernatant (approximately 3 ml) and spread on large 500 cm$^2$ LA (luria agar) plates containing 100 µg/ml Ampicillin+15 µg/ml Tetracycline+1% glucose.
6. The plates were incubated over night at 30° C.
7. The bacteria were collected from the plates by addition of 5 ml of LB containing 100 mg/ml Ampicillin and 15 µg/ml Tetracycline per plate and scraping. The plates were tilted and the solution aspirated.
8. The plates were washed with an additional 3 ml LB medium as above and pooled with the first bacterial suspension in 50 ml Falcon tubes.
9. The bacteria were concentrated by centrifugation for 10 minutes at 2100×g/3000 rpm, Beckman GS6 at room temperature and resuspended in 1 ml of LB containing 100 µg/ml Ampicillin and 15 µg/ml Tetracycline.
10. 500 µl 50% glycerol was added to ml bacterial suspension and the glycerol stock frozen at −80° C.
11. 2×10 ml LB containing 100 µg/ml Ampicillin and 15 µg/ml Tetracycline was infected with 2.5 µl (5 µl) of the glycerol stock of step 10, and grown until OD$_{600}$=0.5.
12. 6×10$^9$ PFU of R408 helper phage were added per ml culture and the cultures were incubated for 30 minutes at 37° C. and 50 rpm.
13. IPTG solution was added to a final concentration of 100 µM (i.e. 2 µl from 0.5 M stock per 10 ml culture) and the cultures were incubated overnight at 25° C. and 175 rpm.

Harvest and Precipitation of Amplified Phage Stocks

1. Bacteria were pelleted for 10 minutes at room temp. 2100×g (3000 rpm, in Beckman GS-6) and the supernatant sterile filtered through 0.2 µm sterile filter.

2. Tubes stemming from the same selection were pooled and the phage precipitated by addition of ¼ volume phage precipitation buffer and incubation for at least 4 hours at 4° C.

3. The tubes were centrifuged for 30 minutes at 4° C. and 13000×g.

4. The pellet was resuspended completely in 100 µl PBS over night at 4° C.

Amplification on Plates for Glycerol Stocks, and Over Night Culture for Minipreps (Following Selection Round 3).

1. 10 ml *E. coli* HB101F' cultures were started (one for each selection to be amplified+one for OD600 measurement) 2.5-3 h before use by addition of 50 µl overnight culture to 10 ml LB containing 15 µg/ml Tetracycline. OD was checked on one culture after approximately 2.5 h.

2. The tubes were infected with half the eluted phage at $OD_{600}$=0.5.

3. The tubes were incubated for 30 minutes at 37° C. and 50 rpm, and for proper phenotyping an additional 30 min at 37° C., 200 rpm.

4. 10 ml warm LB media containing 200 µg/ml Ampicillin were added and the infected bacteria were divided in 2 parts of 10 ml each.

5. In one of the two tubes, the bacteria were concentrated (10 ml) by centrifugation for 10 minutes at 2100×g/3000 rpm, Beckman GS-6 at room temperature, resuspended in a small volume and spread on a 500 cm² LA plate (100 µg/ml ampicillin+15 µg/ml tetracycline+1% glucose) and incubated over night at 30° C.

6. Miniprep: The other 10 ml were spun down and resuspended in 6 ml LB containing 0.1% Glucose and 100 µg/ml Ampicillin and incubated over night at 30° C., 175 rpm.

7. The bacteria were collected from the plates by addition of 5 ml of LB containing 100 µg/ml Ampicillin and 15 µg/ml Tetracycline per plate and scraping. The plates were tilted and the solution aspirated.

8. The plates were washed with an additional 3 ml LB medium as above and pooled with the first bacterial suspension in 50 ml Falcon tubes.

9. The bacteria were concentrated by centrifugation for 10 minutes at 2100×g/3000 rpm, Beckman GS6 at room temperature and resuspended in 1 ml of LB containing 100 µg/ml Ampicillin and 15 µg/ml Tetracycline.

10. 500 µA 50% glycerol was added to 1 ml bacterial suspension and the glycerol stock frozen at −80° C.

11. Purified phage-antibody DNA was obtained by preparing Minipreps from 3 ml of culture according to protocol from the kit manufacturer (BioRad).

To directly assess antibody diversity in the pool generated by BnonT differential biopanning, we used 4-5-4 technology (Margulies et al., 2005) and estimated antibody diversity by determining the number of unique CDRH3 variants in the differentially selected antibody pool.

Deep sequencing by 4-5-4 technology was performed on purified phage-antibody DNA obtained following three rounds of differential biopanning ("B nonT"), identifying a total of 22,497 unique sequences (Table 2). For comparison, conventional screening with Sanger sequencing of phage-antibody DNA from the same BnonT differential biopannings identified only eight unique antibody clones (Table 1).

TABLE 2

Next generation deep sequencing reveals surprisingly great antibody sequence diversity in the antibody pool generated by differential biopanning of target versus non-target cells.

| Replicates per sequence | No. of identified unique sequences | |
|---|---|---|
| | "BnonT" | "DnonT" |
| ≥1 | 22497 | 68060 |
| >1 | 5353 | 25141 |
| >5 | 1589 | 6904 |
| >10 | 996 | 4107 |
| >20 | 593 | 2344 |
| >30 | 419 | 1638 |
| >40 | 318 | 1274 |
| >50 | 258 | 1058 |
| >100 | 136 | 517 |
| >200 | 52 | 225 |

This observation together with our previously reported finding (Fransson et al., 2006) that the vast majority (>99%) of BnonT differentially selected clones were specific for Cancer B cell differentially expressed surface receptors demonstrates that a) the differentially selected antibody pool was in fact highly diversified, and b) that by combining differential biopanning and high-throughput sequencing the number of unique antibody clones specific for differentially expressed surface receptors that can be identified is orders of magnitude greater than that achieved by conventional screening approaches.

In order to demonstrate that differential biopanning followed by high-throughput sequencing can reproducibly be used to generate great numbers of antibodies specific for various surface receptors differentially expressed by various types of target cell, a new differential biopanning/deep sequencing reaction was performed—this time using prostate cancer DU-145 cells as target cells and T cells as non-target cells in the panning reaction "DnonT".

Again, differential biopanning generated a highly target cell specific pool of antibodies (FIG. 3). Deep sequencing by 4-5-4 technology was performed on purified phage-antibody DNA obtained following two rounds (DU-145 vs T) of differential biopanning, identifying a total of 68,060 unique sequences respectively (Table 2).

Figure 9:
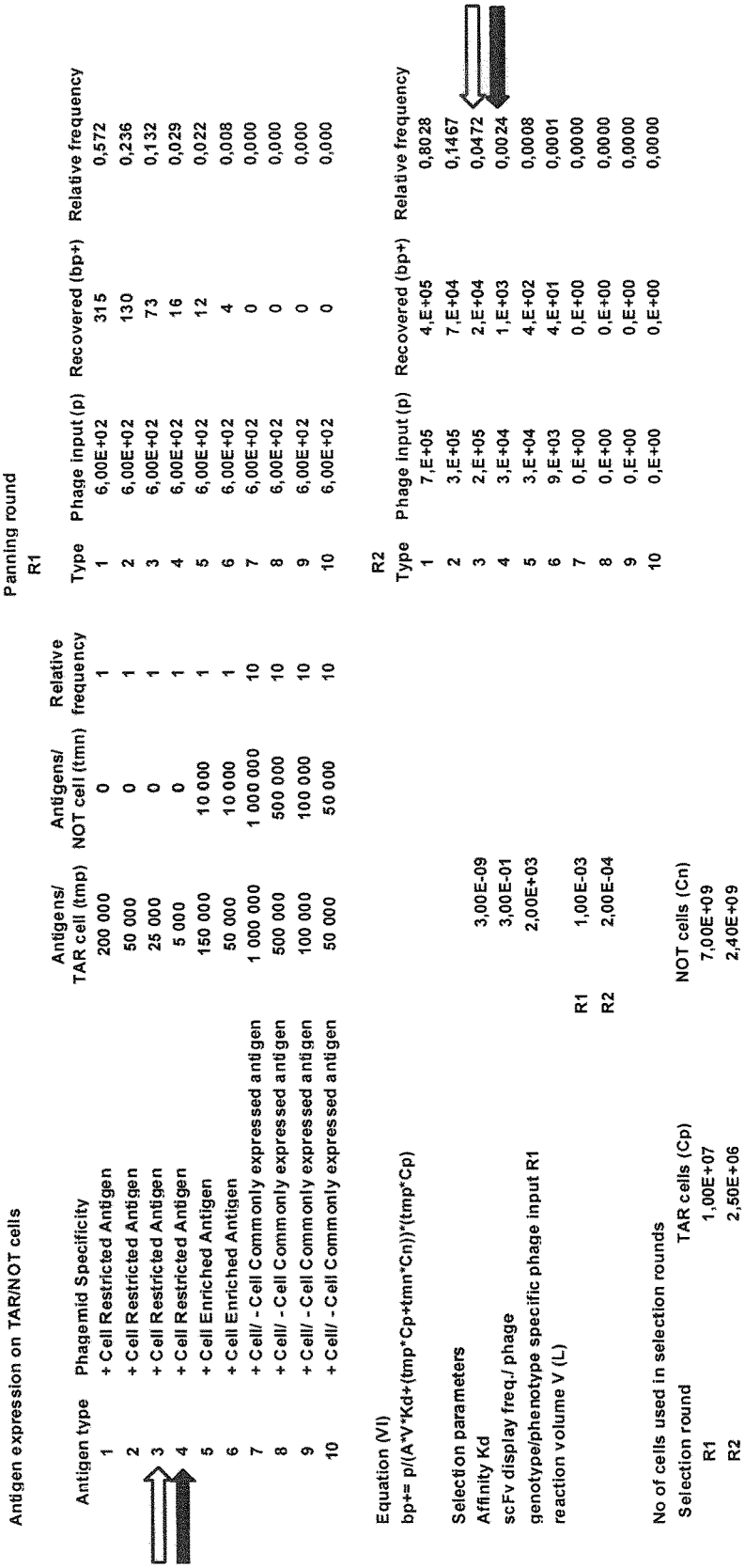

The vast majority of these antibody sequences are likely to be specific for target cell differentially expressed antigens, as indicated by screening of >1400 randomly picked antibody clones for binding to DU-145 versus T cells (FIG. 3B) and by in silico calculations (FIG. 9).

We conclude that combined a) application of differential biopanning to a highly diversified human antibody library followed by b) deep sequencing of the antibody pool generated by differential biopanning, reproducibly generates a much greater number of antibody clones specific for target cell differentially expressed surface receptors than is possible by conventional screening approaches.

EXAMPLE 2—COMBINING DIFFERENTIAL BIOPANNING WITH SUBSEQUENT HIGH-THROUGHPUT SEQUENCING GENERATES A QUALITATIVELY UNIQUE POOL OF ANTIBODY CLONES—INCLUDING THOSE SPECIFIC FOR LOWER EXPRESSED DIFFERENTIALLY EXPRESSED SURFACE RECEPTORS

In silica calculations performed as described in WO2004/023140 and Frendéus, (2006), applying the Law of Mass-action, teach that when applying differential biopanning as performed in the present application (as exemplified in Example 1 using Cancer B cells or Prostate cancer cells as targets), the frequency of retrieved antibody clones in the selected antibody pool will be a direct function of a) their targeted receptors absolute and relative expression on target cell vs non-target cell surfaces and b) their respective affinities for targeted surface receptors.

These calculations further identify that, contrary to the prevailing common view (Hoogenboom, 2002) (Liu et al., 2004; Mutuberria et al., 1999; Osbourn et al., 1998) antibody clones specific for lower expressed surface receptors (e.g. less than 20,000 per cell) as well as those specific for intermediary expressed surface receptors (e.g. expressed at 20,000-50,000 receptors per cell) can and will be selected by differential biopanning as herein described, and will be present in the eluted antibody pool albeit at dramatically lower frequency compared to antibody clones specific for highly expressed differentially expressed surface receptors (FIGS. 2 and 9).

Several approaches have now been used to demonstrate that the antibody pool generated by sequential differential biopanning and deep sequencing is unique in that it contains antibody clones specific for differentially expressed surface receptors expressed at low and intermediary levels, and that increasing the depth of sequencing (i.e. the number of antibody clone sequences analysed) results in identification of antibodies specific for differentially expressed surface receptors expressed at decreasing (lower) levels on target (vs non-target) cells.

Firstly, we demonstrated that the antibody pool selected by differential biopanning does contain antibody clones that are specific for low and intermediary differentially expressed surface receptors (FIGS. 4, 5 and 6).

By subjecting the differentially selected antibody pool to one additional selection with extracellular domains (ECD) of surface receptors verified to be differentially expressed by target cells vs non-target cells, and verified to be expressed at low to intermediary levels on target cells by scatchard plot and FACS analyses (FIGS. 4 and 5 TBG) we isolated several (twelve) antibody clones specific for different low and intermediary expressed surface receptors from the differentially expressed antibody pool including those specific for CD24, CD130 and HER2 surface receptors (FIG. 6).

One isolated antibody against each receptor was converted to IgG format and used for scatchard and FACS analyses, revealing expression levels of 6,000-100,000 receptors/cell (Table 3, FIGS. 4 and 5).

TABLE 3

Scatchard analyses of DU145 cells with antibodies against three surface receptors reveals expression levels of 6,000-100,000 receptors/cell.

| Receptor | Antibody KD (nM) | Epitope/cell |
|---|---|---|
| CD130 | 0.8 | 6,300 |
| CD24 | 5.6 | 8,400 |
| HER-2 | 47 | 110,000 |

Experimental Methods
Selection with Extracellular Domains (ECD) of Surface Receptors
Reaction Parameters Phages eluted and amplified following two rounds of differential biopanning (DU-145 vs T, "DnonT") were precipitated and resuspended in PBS. 100 µl (corresponding to $2.4 \times 10^{11}$ phages) were used in the $3^{rd}$ selection round.

Total reaction volume 1.0 ml

In the selection, phages were enriched for binders to three surface-localized proteins: CD24, CD130 and HER2.
Method—ECD Selections 50 pmole of each protein (see above) was used to coat 4 polystyrene balls (Polysciences, cat no 17175-100) in a reaction volume of 1 ml 0.1M sodium carbonate buffer, pH 9.5. Coating was performed in an eppendorf tube at room temperature for 1 h with end-over-end rotation and a subsequent overnight incubation step at 4° C. without rotation.

The coated balls were washed once with 1 ml TPBSB-3% (PBS containing 3% BSA, 0.05% Tween-20 and 0.02% $NaN_3$), and blocked by a 1 h incubation step with 1 ml TPBSB-5% (PBS containing 5% BSA, 0.05% Tween-20 and 0.02% $NaN_3$) at room temperature for 1 h with end-over-end rotation. Following washing with 1 ml TPBSB-3%, the balls were transferred to a fresh eppendorf tube and phages were added to the blocked balls (in a total volume of 1 ml TPBSB-3%). The mixture was incubated overnight at 4° C. with end-over-end rotation.

To remove unbound phages, the balls were washed three times with 1 ml TPBSB-3%, followed by three washes with 10 ml TPBS (PBS containing 0.05% Tween-20 and 0.02% $NaN_3$) and three washes with 10 ml PBS. Prior to the TPBS wash, the balls were collected using a strainer and transferred to a fresh 50 ml tube, in which all subsequent wash steps were performed. To facilitate the washing procedure, each washing step was followed by a three minute incubation step at room temperature with end-over-end rotation.

The washed balls were collected using a strainer and transferred to a fresh eppendorf tube. Bound phages were eluted by incubating the balls with 400 µl 0.5% trypsin at room temperature for 30 minutes with end-over-end rotation, followed by addition of 40 µl aprotinin (2 mg/ml) to inactivate the trypsin. The trypsin/aprotinin mixture containing the eluted phages was transferred to an eppendorf tube and the balls were washed with 200 µl PBS, which was subsequently pooled with the eluted phages, resulting in a total volume of 640 µl.
Amplification on Plates for Glycerol Stocks, and Over Night Culture for Minipreps These aspects of the method were performed as described in Example 1.
Conversion from Phage-Bound to Soluble scFv Format This is a conversion method where the scFv fragment is restricted from the phagemid ($Amp^R$) and inserted in a vector, pKscFv-3×FH, which carries a gene encoding kanamycin resistance.
Material:
AvrII (4 U/µl, New England Biolabs Cat No R0174)
10× NEBuffer2 (New England Biolabs Cat No B7002S)
MQ water
SfiI (20 U/µl, New England Biolabs Cat No R0123)
10×BSA (100×BSA New England Biolabs Cat No B9001S diluted 10× in MQ water)
QIAquick PCR purification kit (Qiagen Cat No 28104)
SfiI/AvrII digested pKscFv 3×FH
T4 DNA Ligase (1 U/µl, Invitrogen Cat No 15224-017)
5× T4 DNA ligase buffer (Invitrogen, Cat No P/N Y90001)
Digestion of Phagemid DNA
  Prepare digestion reactions using the phagemid minipreps:
    2 µg Phagemid miniprep
    1 µl⇒ 4 U AvrII
    2 µl⇒ 1×10× NEBuffer2
    MQ $H_2O$ to 20 µl total volume
    Incubate at 37° C. for 2 hours.

Proceed with SfiI digestion. To the digestion mix from above add:
  1 µl ⇒ 1×10× NEBuffer2
  3 µl ⇒ 1×10×BSA
  1 µl ⇒ 20 U SfiI
  5 µl MQ H$_2$O ⇒ 30 µl total volume
Incubate at 50° C. for 2 hours.

Purify the digested DNA using QIAquick PCR Purification Kit according to vendor's instructions. Use 50 µl water for elution. Approximately 50 µl with a total concentration of 40 ng/µl will be retrieved (assuming 100% recovery).

Ligation

Set up the following ligation mix:
  0.6 µl ⇒ 60 ng SfiI/AvrII digested pKscFv 3×FH
  6 µl ⇒ 240 ng SfiI/AvrII digested/purified Phagemid miniprep
  5 µl ⇒ 1×5× ligase buffer
  1 µl ⇒ 1 U T4 DNA Ligase
  12.4 µl MQ H$_2$O ⇒ 25 µl total volume
Incubate at 16° C. over night.
Store at −20° C. until use.

Transformation

The ligate produced above was transformed into *E. coli* TOP10.

One tube (100 µl/tube)/ligate of chemically competent TOP10 cells were thawed on ice. 10 ng ligate were added per tube and the tubes were incubated on ice for 30 min.

The tubes were then incubated at 42° C. (water bath) for 90 s, and further incubated on ice for 5 min.

900 µl LB was added to each tube and the tubes were incubated at 37° C., 1 h, 200 rpm.

The content of each tube was spread on one 500 cm$^2$ LA plate (100 µg/ml Kanamycin+1% glucose) and incubated overnight at 37° C.

Colony Picking

A total of 1152 clones were picked from each selection (CD24, CD130 and HER2) from the large LA plates to 3×384 well microtitre plates/selection (totally 9 plates) using a Genetix "Q-bot" colony picking system.
1. Mix LB media, 20 µg/ml of Kanamycin and glucose 1%.
2. Fill the plates (Greiner Flat 384 well 781101) with media, 60 µl/well.
3. Pick colonies with the Q-Bot according to the protocol.

Expression of Clones in 384 Well Format
1. Fill the expression plate (Greiner Flat 384 well 781101) with media 50 µl/well including Kanamycin 20 µg/ml.
2. Inoculate the expression plate with 5 µl/well from the master plate.
3. Incubate the expression plate at 37° C., 600 rpm for 3.5 h.
4. Induce the production of scFv with 10 µl/well of media including Kanamycin 20 µg/ml and 2.5 mM IPTG.
5. Incubate the expression plate for 10 h at 37° C., 600 rpm.
6. Store the expression plate at +4° C.

Screening of Clones 384 Well

Material:
CD24-GST (0.11 mg/ml), Abnova Cat No H00000943-H01
HER-2-Fc (0.1 mg/ml in PBS), R&D Systems Cat No 1129-ER
CD130 (0.2 mg/ml), R&D Systems Cat No 228-GP
human IgG (6.2 mg/ml), Sigma Cat No 12511
Anti His-HRP, R&D Systems Cat No MAB050H
Anti FLAG-AP, Sigma Cat No A9469
Fish gelatin, Sigma Cat No G7765
Supersignal ELISA Pico, Thermo Scientific Cat No 37069
Tropix CDP Star Emerald II, Applied Biosystems Cat No T2388C Procedure:

Day 1 Coating
1. Coat the plates (Greiner 384 well plate white HB 781074) with:
  CD24 0.4 pmole/well
  HER2 0.8 pmole/well
  CD130 0.9 pmole/well
  hIgG (non-target) 1 pmole/well
  diluted in 0.1 M Sodium Carbonate, pH 9.5, 50 µl/well. Incubate the plates over night at +4° C.

Day 2
2. Wash the plates with 1×PBS, 0.05% (v/v) Tween-20 three times.
3. Add PBS+0.05% Tween-20+0.45% Fish gelatine, 40 µl/well.
4. Add the expressed scFv, 10 µl/well and incubate the plate at room temperature for 1 hour.
5. Wash the plates as above.
6. Add the secondary antibody diluted in PBS+0.05% Tween-20+0.45% Fish gelatine; α-HIS-HRP diluted 1:4000 to plates coated with CD24, CD130 and hIgG, α-FLAG-AP, diluted 1:25000 to plates coated with HER2 and hIgG, 50 µl/well and incubate the plate for 1 hour at room temperature. Note: Double plates for hIgG.
7. Wash the plates as above. Wash the plates with 20 mM Tris-HCl, 10 mM MgCl$_2$, pH 9.8 three times.
8. Add substrate;
  To plates with anti-His-HRP add Pierce Supersignal ELISA Pico diluted 1:20 in 20 mM Tris-HCl, 10 mM MgCl$_2$, pH 9.8, 50 µl/well and incubate the plate for 10 min at room temperature.
  To plates with anti-Flag add Tropix CDP Star Emerald II diluted 1:20 in 20 mM Tris-HCl, 10 mM MgCl$_2$, pH 9.8, 50 µl/well and incubate the plate for 30 min at room temperature.
9. Read the plates.

FACS Analysis of DU145 Receptor Expression after IFN-γ Stimulation

Material
Jurkat cells
DU145 cells
Trypsin-EDTA (Invitrogen Cat No 25300-054)
rh-IFN-γ (R&D Systems Cat No 285-IF)
Mouse IgG Block (Jackson Immunoresearch Cat No 015-000-002)
FACS buffer (Gibco Cat No 14040 PBS w/o Ca and Mg+0, 5% BSA)
Zenon Alexa Fluor 647 Human IgG Labeling Kit (Invitrogen Cat No Z25408)

INF-γ Stimulation

DU145 cells were stimulated with 250IE INF-γ for 24 h. The cells were harvested with cell dissociation buffer.

Method Flow Cytometer

The cells were washed once in FACS buffer and blocking was conducted using 50 µg/ml mouse IgG in FACS buffer on ice for 10 minutes. Meanwhile, antibodies were labeled with Zenon AF 647 according to the manufacturer's instructions.

50 µl cell suspension (approx 500,000 cells) were transferred to the FACS tubes and 50 µl labeled antibody was added before incubation for 1 h on ice.

FACS buffer was then used to wash the cells and the resulting suspension was analysed in flowcytometer (BD Bioscience, FACS Calibur).

Scatchard Analysis of DU145 Receptor Expression after IFN-γ Stimulation
INF-γ Stimulation DU145 cells were stimulated with 250IE INF-γ for 24 h. The cells were harvested with cell dissociation buffer.

Scatchard Analyses

The antibodies were labelled with $^{125}$I using free Iodine and test tubes pre-coated with the oxidant reagent Iodogen (1,3,4,6-tetrachloro-3α,6α-diphenylglycoluri, Thermo scientific), according to manufactures instruction. Briefly 200 µg of antibody was labeled for 10 minutes in PBS and free iodine was removed using a small disposable desalting column (NAP 5, GE Healthcare Life science). Labelled antibody had a specific activity of approximately 2.5 µCi/µg antibody and contained less than 1% free Iodine as estimated with paper chromatography.

$0.5 \times 10^6$ cells were incubated for 2.5 h (on ice bath) with different concentrations of $^{125}$I-labelled antibody. Free non-binding antibody (F) was separated from cell bound antibody (B) by centrifugation through a 40% Ficoll-cushion and samples were analysed in a gamma counter.

approaches (Table 4 and data not shown). In contrast, no antibodies specific for low expressed surface receptors were identified by conventional screening of up to 813 randomly picked clones (Table 4). Strikingly, and in stark contrast, antibodies specific for the low expressed CD24, and CD130 surface receptors were identified by deep sequencing.

The effect of increasing sequencing depth on retrieved antibodies' specificity for high, intermediary and low expressed differentially expressed surface receptors was examined as follows:

Antibody clone sequences from three randomly selected pools of binders of increasing size (91 clones, 255 clones, and 813 clones, respectively) were determined. Thereafter, clones that were found in all three pools ("abundant clones)", found only in the two larger pools ("less frequent clones"), or only in the largest pool ("rare clones") were analyzed for binding to DU145 cells by FACS.

Mean target expression levels of receptors targeted by abundant, less frequent, and rare clones decreased with decreasing prevalence in the differentially selected antibody pool (FIG. 7), demonstrating that increasing sequence depth

TABLE 4

(associated with FIG. 6). Comprehensive identification of antibodies specific for low and intermediary expressed surface receptors requires deep sequencing of the differentially selected antibody pool.

| | Sequencing | | High expressed receptors (Expression level) | | Low expressed receptors (Expression level) | |
|---|---|---|---|---|---|---|
| | Type of sequencing | # of sequenced clones | CD54 (250,000) | HER2 (100,000) | CD24 (8,000) | CD130 (6,000) |
| Previously described differential biopanning method | Coventional (Sanger) | 91 | 47 | 2 | - | - |
| | | 255 | ND | - | - | - |
| | | 813 | ND | 4 | - | - |
| Current reversed screening method | Deep (4-5-4) | ~290000 sequences | ND | 511 | 3 | 5 |

The table shows the number of retrieved antibody clones specific for each expressed surface receptor as a function of the number of antibody clones sequenced. Receptor specificities of individual antibody clones were determined as described in FIG. 6.

Analogous screening of 96 clones from the differentially selected antibody pool identified 47 sequences specific for the highly expressed surface receptor ICAM-1 (Table 4).

We next asked whether antibodies (sequences) specific for surface receptors expressed at high, intermediary and low levels, respectively, were identified by sequencing of 91, 255, or 813 randomly picked antibody clones or following deep sequencing of ~290,000 randomly picked antibody clones.

CD54 was identified as a high expressed surface receptor with 250,000 copies/cell by scatchard analyses (data not shown). Screening of 96 clones from the differentially selected antibody pool "DnonT" identified 47 clones specific for CD54 (Table 4). HER2 with 100,000 copies/cell represents a high expressed surface receptor and CD24 with 8,000 and CD130 with 6,000 copies/cell represents low expressed surface receptors (FIGS. 4 and 5).

Antibodies (sequences) specific for the highly expressed surface receptor ICAM-1 were identified by all screening results in identification of antibodies specific for differentially expressed surface receptors expressed at decreasing (lower) levels on target (vs non-target) cells.

EXAMPLE 3—DERIVING THE DIFFERENTIAL BIOPANNING EQUATIONS

Applying the Universal Law of Mass Action (LMA), the number of ligands needed to isolate anti-ligands to low expression ligands and/or differentially expressed ligands from display libraries of high diversity may be calculated.

The LMA states that the non-covalent (hydrogen bonding, electrostatic, Van der Waals or hydrophobic forces), reversible binding between an anti-ligand A and its target ligand T, and their complex AT is given by the equilibrium interaction A+T⇔ AT with the equilibrium dissociation constant or affinity $K_d = [A][T]/[AT]$.

The equilibrium interaction between anti-ligands with identical specificity (A) for a target ligand (T) may be described as Bound A (bA) ⇔ free A (fA) + free T (fT)
with $$Kd = [fA] \times \frac{[fT]}{[bA]} \quad (I)$$

It is known that the total A or T is the sum of free and bound A or T i.e. [A](Total A)=[fA]+[bA], and [T](Total T)=[fT]+[bA]

Therefore in (I) replacing [fA] by [A]−[bA], and [fT] by [T]−[bA]

$$K_d = ([A] - [bA]) \times \frac{[T] - [bA]}{[bA]} \quad (II)$$

Which is rearranged to form $(K_d \times [bA]) = ([A][T] - [A][bA]) - ([T][bA] - [bA]^2)$ $0 = [bA]^2 - ([A] + [T] + K_d)[bA] + [A][T]$ This simultaneous equation has the solution $$[bA] = \frac{([A] + [T] + K_d)}{2} \pm \sqrt{\frac{([A] + [T] + K_d)^2}{4} - [A][T]}$$

where the negative root is the relevant one:

$$[bA] = \frac{([A] + [T] + K_d)}{2} - \sqrt{\frac{([A] + [T] + K_d)^2}{4} - [A][T]}$$

Substituting concentrations for particle numbers/the number of particles per mole (C)/unit of volume (V) yields $$\frac{bA}{(C \times V)} =$$

$$\frac{\left(\frac{A}{(C \times V)} + \frac{T}{(C \times V)} + K_d\right)}{2} - \sqrt{\frac{\left(\frac{A}{(C \times V)} + \frac{T}{(C \times V)} + K_d\right)^2}{4} - \frac{AT}{(C \times V)^2}}$$

and simplified to $$bA = \frac{(A + T + (K_d) \times (C \times V))}{2} - \sqrt{\frac{(A + T + (K_d) \times (C \times V))^2}{4} - AT} \quad (III)$$

where
A=total number of anti-ligands A
T=total number of ligands T
V=the reaction volume (liters)
C=Avogadro's constant (6.022×10$^{23}$ particles/mole)

Given that the LMA applies to each reaction between different anti-ligands with given affinity and specificity for their respective target ligands, the number of anti-ligands bound to ligands following a selection process may be calculated by applying the LMA and equation (III).

Furthermore, if there is no qualitative difference between the anti-ligands associated with the populations of subtractor or target ligands, i.e. that there is no change in the physico-chemical properties of the ligand during the method, then the number of anti-ligands that have bound to target ligands at equilibrium will be equal to the total number of bound anti-ligands multiplied by the ratio of target ligands on target ligand constructs to total ligand (subtractor and target ligand):
Introducing
  $C_P$=the number of target ligand constructs
  $C_S$=the number of subtractor ligand constructs
  $T_P$=the number of T ligands on $C_P$
  $T_S$=the number of T ligands on $C_S$
If target and subtractor constructs are mixed then the total number of ligands will be:

$T_{Tot} = (T_P \times C_P + T_S \times C_S)$

And the number of anti-ligands (A) bound to the positive constructs at equilibrium ($bA_P$) is given by:

$$bA_P = bA \times \frac{(T_P \times C_P)}{T_{Tot}} \quad (IV)$$

Furthermore the combination of equations (III) and (IV) yields $$bA_P = \left\{ \frac{(A + T + (K_d) \times (C \times V))}{2} - \sqrt{\frac{(A + T + (K_d) \times (C \times V))^2}{4} - A \times T} \right\} \times \left\{ \frac{(T_p \times C_p)}{((T_p \times C_p) + (T_s \times C_s))} \right\} \quad (V)$$

EXAMPLE 4—OPTIMISING LIGAND CONCENTRATIONS

The equations exemplified in example 1 show that utilisation of high concentrations of both the first subtractor ligand and the second target ligand is instrumental in the efficient retrieval of anti-ligands with specificity for low expression and differentially expressed ligands, as well as for the reduction of anti-ligands with specificity for commonly expressed ligands.

Ligand concentration may be increased by several means. In all cases ligand concentration is increased by moving from two-dimensional coupling of ligand (coupling to a two-dimensional solid-phase) to use of ligand free in suspension or solution (three-dimensional).

In cases where binding is dependent on the ligand being used in its native configuration, such as for cell surface ligands, then ligand concentration is maximised by increasing the ratio of ligand construct surface area to ligand construct volume.

For example, cell surface antigens may be used in the form of small plasma membrane vesicles free in suspension, as opposed to using whole cells fixed to a 2-dimensional surface. This has the additional advantage of increasing the stability of the ligand in suspension or solution, thus promoting the ligand-anti-ligand equilibrium interaction.

If the ligand source has a spherical (or substantially spherical) form, this is described mathematically by the following equation:

$$Ap/Vp=(4\pi r^2)/(4\pi r^3/3)=\pi/3r$$

Where
Ap=sphere area
Vp=sphere volume
i.e. the smaller the radius of the sphere, the greater the ratio of ligands/volume and the more particulate (suspension like) the ligand.

EXAMPLE 5—PREFERRED EMBODIMENT

In a preferred aspect the invention is used to isolate anti-ligands with specificity for cell surface antigens in their native configuration and independent of their nature (protein, carbohydrate, lipid, complex). Additionally the antigens being bound are those upregulated or uniquely expressed on one cell type compared to another (e.g. transformed cancer cell, viral/microbial/parasite/fungal infected cell or other agonist stimulated or infection activated cell versus control cells).

When utilised for selection of antibody derived anti-ligands (e.g. scFv-, Fab-, or Fv-encoding anti-ligands), the method, simultaneously with the screening process, generates therapeutic antibody candidates that react with target antigen in its native configuration at the cell membrane.

Because such large concentrations of antigen are needed, antigen is used in a form that does not impair the equilibrium reaction. Therefore, antigen is used in forms that occupy minimal space and impose little increase in viscosity and shearing forces.

For example, when anti-ligands to cell surface antigens are sought, a competition biopanning process utilising target whole cells and excess subtractor cell membranes mixed with members of a highly diversified molecular anti-ligand library may be used, followed by density separation on a Ficoll or Percoll/bovine serum albumin gradient and selective isolation of target cells and anti-ligands specific for target cell upregulated and unique antigens.

In this methodology the target ligand (antigen) population is in the form of whole cells (high density) and the subtractor ligand (antigen) is in the form of plasma membrane vesicles or enucleated cells (low density).

The target and subtractor antigen populations are mixed with members of a highly diverse molecular library in a controlled manner based on the equations described herein.

For example, $5\times10^7$ target whole cells are mixed with cell membrane vesicles of $1\times10^{10}$ subtractor cells and mixed with members from a highly diversified library at an anti-ligand specific copy number of 200 (typically producing anti-ligands of $Kd=10^{-8}M$ when selecting on pure antigen), one can expect to isolate anti-ligands specific for 10-fold or greater upregulated antigens including those expressed at such low densities as 10,000 per target cell.

The reaction is incubated to reach equilibrium. Following competitive biopanning, library members bound to the target population are separated from unbound anti-ligands and those anti-ligands bound to control subtractor antigen by density centrifugation separation, resulting in enrichment of phage specific for highly expressed antigens present among the studied population.

Where the desired target antigen expression is higher in the subtractor population the process is reversed, so that the subtractor ligand population becomes target ligand population and vice versa.

Besides generating anti-ligands with specificity for differentially expressed and unique ligands, use of different density separation means on a density gradient, offers several advantages including:

Physical and spatial separation of anti-ligands complexed to positive ligand from unbound anti-ligands and anti-ligands with specificity for ligand found in the control population.

Ficoll washing increases shear force. Hence, such washing is more efficient and less washing repetitions (panning rounds) are needed; and there is minimal dissociation of specifically bound (higher affinity) anti-ligands of interest.

Does not require tagging or chemical modification of cells (compare FACS (fluorescence activated cell sorter) or MACS (magnetic activated cell sorter) based competitive biopanning) that might alter cell surface ligand configuration/conformation and/or composition.

EXAMPLE 6—ALL MEMBRANE VESICLES AS SEPARATION MEANS

Whole cells can be replaced by membrane vesicles produced in a higher density media, allowing for even higher concentrations of ligand to be utilized without compromising the equilibrium reaction.

EXAMPLE 7—TESTING THE EFFECTS OF STIMULI ON LIGAND UP/DOWN-REGULATION

A further embodiment of the invention may be used to isolate anti-ligands with specificity for cellular ligands that are expressed at a very low density in only a small number of cells within the cell population being studied.

For example, a certain stimulus may be suspected to trigger the upregulation or downregulation of a cell surface antigen present on an unknown cell subpopulation present in blood.

Cells derived from whole blood exposed to this stimulus may be mixed with plasma membranes derived from whole blood prior to exposure to the stimulus, and a competitive biopanning reaction analogous to that described above.

EXAMPLE-8—DIAGNOSTIC USE OF THE SCREENING METHOD

A further example of the invention, allows anti-ligands against ligands present at different abundance in biological samples (e.g. plasma, urine, cerebrospinal fluid) to be isolated from highly diversified molecular libraries. Such anti-ligands may subsequently be used for, e.g., protein expression analysis and identification of potential biomarkers.

If sufficiently high concentrations of ligands are used, the method of the invention allows for selective isolation of anti-ligands against up-regulated or unique ligands when comparing protein composition in two different samples. This ultimately allows for isolation of anti-ligands specific for ligands that are more abundant in one population compared to another population, in a manner that is independent of the relative ligand concentrations within the positive ligand population.

Due to the extreme concentrations of ligand needed to accomplish the latter, ligand should preferably be used in suspension or solution. For example, target population ligand can be split and tagged at several different positions to minimise destruction and eradication of relevant ligands, white subtractor population ligands can be used untagged or mock treated. Tagging of the positive ligand population provides a means for subsequent retrieval of positive population ligands and binders bound to positive population ligands only by use of tagged ligand complexed with e.g. counter tagged magnetic beads.

An application of this method would be to pool plasma samples from a population of patients with a certain illness and compare to a plasma samples from a control population. In this case the patient plasma samples would be split and tagged, and the control population would be untagged.

REFERENCES

Barbas C F, Kang As, Lerner R A and Benkovic S J, (1991), Assembly of combinatorial antibody libraries on phage surfaces: the gene III site. *Proc. Natl. Acad. Sci. USA* 88, 7978-7982;

Beck et al. (2010). Strategies and challenges for the next generation of therapeutic antibodies. Nat Rev Immunol 10, 345-352

Beers et al. (2008). Type II (tositumomab) anti-CD20 monoclonal antibody out performs type I (rituximab-like) reagents in B-cell depletion regardless of complement activation. Blood 112, 4170-4177.

Bentley D R, et al. Accurate whole human genome sequencing using reversible terminator chemistry. Nature. 2008; 456: 53-59.

Carlsson, R. et al. (1988) Binding of staphylococcal enterotoxin A to accessory cells is a requirement for its ability to activate human T cells. *J Immunol* 140, 2484.

Chiswell D J and McCafferty J, (1992), Phage antibodies: will new 'coliclonal' antibodies replace monoclonal antibodies? *Trends Biotechnol.* 10, 80-84

Clackson T, Hoogenboom H R, Griffiths A D and Winter G, (1991), Making antibody fragments using phage display libraries. *Nature* 352, 624-628

Cragg, M. S., and Glennie, M. J. (2004). Antibody specificity controls in vivo effector mechanisms of anti-CD20 reagents. Blood 103, 2738-2743

Dower, W. J., CWIRLA, S. E. and N. V., A. T. (1991) Recombinant Library Screening Methods. In: *World Intellectual Property Organization.* SMITH, W. M., United States.

Drmanac R, et al. Human Genome Sequencing Using Unchained Base Reads on Self-assembling DNA Nanoarrays. Science 2010; 327: 78-81

Felici F, Luzzago A, Manaci P, Nicosia A, Sollazzo M and Traboni C, (1995), Peptide and protein display on the surface of filamentous bacteriophage. *Biotechnol. Annual Rev.* 1, 149-183

Francisco, J. A., Stathopoulos, C., Warren, R. A., Kilburn, D. G. and Georgiou, G. (1993) Specific adhesion and hydrolysis of cellulose by intact *Escherichia coli* expressing surface anchored cellulase or cellulose binding domains. *Biotechnology* (N Y) 11, 491.

Fransson, J., Tornberg, U. C., Borrebaeck, C. A., Carlsson, R., and Frendeus, B. (2006). Rapid induction of apoptosis in B-cell lymphoma by functionally isolated human antibodies. Int J Cancer 119, 349-358.

Gao, C., Lin, C. H., Lo, C. H., Mao, S., Wirsching, P., Lerner, R. A. and Janda, K. D. (1997) Making chemistry selectable by linking it to infectivity. *Proc Natl Acad Sci USA* 94, 11777.

Hanes, J. and Pluckthun, A. (1997) In vitro selection and evolution of functional proteins by using ribosome display. *Proc Natl Acad Sci USA* 94, 4937.

Harris T D, et al. Single-molecule DNA sequencing of a viral genome. Science 2008; 320:106-109.

He, M. and Taussig, M. J. (1997) Antibody-ribosome-mRNA (ARM) complexes as efficient selection particles for in vitro display and evolution of antibody combining sites. *Nucleic Acids Res* 25, 5132.

Hoogenboom H R and Winter G, (1992), By-passing immunisation. Human antibodies from synthetic repertoires of germline VH gene segments rearranged in vitro. *J. Mol. Biol.* 227, 381-388).

Hoogenboom H R, deBruine A P, Hutton S E, Hoet R M, Arends J W and Rooves R C, (1998), Antibody phage display technology and its application. *Immunotechnology* 4(1), 1-20.

Hoogenboom, H. R. (2002). Overview of antibody phage display technology and its applications. In Methods in Molecular Biology P. M. O'Brien, and R. Aitken, eds. (Totowa, N.J.: Humana Press Inc.), pp. 1-37.

Jacobsson, K. and Frykberg, L. (1995) Cloning of ligand-binding domains of bacterial receptors by phage display. *Biotechniques* 18, 878.

Katz B A, (1997), Structural and mechanistic determinants of affinity and specificity of ligands discovered or engineered by peptide display. *Annual Rev. Biophys. Biomol. Struct.* 26, 27-45

Kay B K and Paul J I, (1996), High-throughput screening strategies to identify inhibitors of protein-protein interactions. *Mol. Divers.* 1, 139-140).

Koide, A., Bailey, C. W., Huang, X. and Koide, S. (1998) The fibronectin type III domain as a scaffold for novel binding proteins. *J Mol Biol* 284, 1141.

Liu et al. (2004). Mapping tumor epitope space by direct selection of single-chain Fv antibody libraries on prostate cancer cells. Cancer Res 64, 704-710.

Lundquist P M, et al. Parallel confocal detection of single molecules in real time. Optics Letters 2008; 33: 1026-1028.

Margulies M, et al. Genome sequencing in microfabricated high-density picoliter reactors. Nature 2005; 437: 376-380.

Markland, W., Roberts, B. L., Saxena, M. J., Guterman, S. K. and Ladner, R. C. (1991) Design, construction and function of a multicopy display vector using fusions to the major coat protein of bacteriophage M13. *Gene* 109, 13.

Marks J D, Hoogenboom H R, Bonnert T P, McCafferty J, Griffiths A D and Winter G, (1991), By-passing immunisation. Human antibodies from V-gene libraries displayed on phage. *J. Mol. Biol.* 222, 581-597

Mattheakis, L. C., Bhatt, R. R. and Dower, W. J. (1994) An in vitro polysome display system for identifying ligands from very large peptide libraries. *Proc Natl Acad Sci USA* 91, 9022.

McCafferty, J., Griffiths, A. D., Winter, G. and Chiswell, D. J. (1990) Phage antibodies: filamentous phage displaying antibody variable domains. *Nature* 348, 552.

Mutuberria et al. (1999). Model systems to study the parameters determining the success of phage antibody selections on complex antigens. J Immunol Methods 231, 65-81.

Osbourn et al. (1998). Pathfinder selection: in situ isolation of novel antibodies. Immunotechnology 3, 293-302.

Shendure J, et al. Accurate multiplex polony sequencing of an evolved bacterial genome. Science 2005; 309: 1728-1732.

Siegel et al. (1997). Isolation of cell surface-specific human monoclonal antibodies using phage display and magnetically-activated cell sorting: applications in immunohematology. *J Immunol Methods* 206, 73-85

Smith, G. P. (1985) Filamentous fusion phage: novel expression vectors that display cloned antigens on the virion surface. *Science* 228, 1315.

Smith, G. P. and Scott, J. K. (1993) Libraries of peptides and proteins displayed on filamentous phage. *Methods Enzymol* 217, 228.

Stahl et al. (1989) A dual expression system for the generation, analysis and purification of antibodies to a repeated sequence of the *Plasmodium falciparum* antigen Pf155/RESA. *J Immunol Methods* 124, 43.

Weng, S., Gu, K., Hammond, P. W., Lohse, P., Rise, C., Wagner, R. W., Wright, M. C. and Kuimelis, R. G. (2002) Generating addressable protein microarrays with PROfusion covalent mRNA-protein fusion technology. *Proteomics* 2, 48.

Williams, B. R. and Sharon, J. (2002) Polyclonal anti-colorectal cancer Fab phage display library selected in one round using density gradient centrifugation to separate antigen-bound and free phage. *Immunol Lett* 81, 141.

Winter and McCafferty (1996) *Phage display of peptides and proteins: a laboratory manual* Ed Kay, Academic Press, Inc ISBN 0-12-402380-0

Winter, G., Griffiths, A. D., Hawkins, R. E. and Hoogenboom, H. R. (1994) Making antibodies by phage display technology. *Annu Rev Immunol* 12, 433.

The invention claimed is:

1. A method of isolating at least one anti-ligand to at least one differentially-expressed target ligand, said method comprising the steps of:
   (a) performing differential biopanning on a library of anti-ligands so as to isolate at least one anti-ligand against said target ligand, wherein said differential biopanning comprises:
      (i) providing a first population of ligands fixed to or incorporated in a subtractor ligand construct;
      (ii) providing a second population of ligands comprising the same ligands as step (i), fixed to or incorporated in a target ligand construct;
      (iii) determining an amount of said subtractor ligand construct and an amount of said target ligand construct so as to permit isolation of said at least one anti-ligand to said differentially-expressed target ligand;
      (iv) exposing said library of anti-ligands to said amount of said subtractor ligand construct and said amount of said target ligand construct determined in step (iii) to permit binding of anti-ligands to ligands; and,
      (v) isolating anti-ligands bound to said target ligand construct; and,
   (b) performing next generation deep sequencing on anti-ligands isolated during step (a).

2. The method of claim 1 further comprising the step of:
   (c) performing confirmatory screening for antibody specificity for the differentially-expressed target ligand, wherein said anti-ligand is an antibody.

3. The method of claim 1 wherein the differential biopanning sub-step (iii) is carried out using one or more equations derived from the universal law of mass action $$\frac{[C]^c [d]^d}{[A]^a [B]^b} = K_{eq}$$

where:
A, B, C & D = are the participants in the reaction (reactants and products)
a, b, c, & d = the coefficients necessary for a balanced chemical equation so as to permit isolation of said at least one anti-ligand to differentially expressed target ligand.

4. The method of claim 1 wherein the next generation deep sequencing is conducted by 454 sequencing, Illumina, SOLiD methods or the Helicos system.

5. The method of claim 2 wherein the confirmatory screening step is conducted by Flow-cytometry, FMAT, ELISA, MSD or CBA.

6. The method of claim 1 wherein the ligand is not expressed on one of either the target ligand construct or the subtractor ligand construct.

7. The method of claim 1 comprising a further step of releasing the anti-ligand from the ligand.

8. The method of claim 1 whereby sub-steps (i) to (v) are conducted in parallel to isolate a plurality of anti-ligands to a plurality of different ligands.

9. The method of claim 1 whereby sub-steps (i) to (v) are repeated one or more times.

10. The method of claim 1 wherein the amount of one of the subtractor construct or target construct is provided in excess of the amount of the other of the subtractor construct or target construct.

11. The method of claim 10 where the excess of ligand is between 10 and 1000 fold, or 2 and 10 fold, or 1000 and 1,000,000 fold.

12. The method of claim 3 wherein said one or more equations are either:

$$bA = \frac{(A + T + (K_d) \times (C \times V))}{2} - \sqrt{\frac{(A + T + (K_d) \times (C \times V))^2}{4} - A \times T}$$

where
bA = Bound anti-ligand
A = Total number of anti-ligand
T = Total number of ligands
C = Avogadro's constant (6.022×10$^{23}$ particles/mole)
V = Reaction volume (liters)
$K_d$ = Equilibrium dissociation constant or $$bA = \left\{ \frac{(A + T + (K_d) \times (C \times V))}{2} - \sqrt{\frac{(A + T + (K_d) \times (C \times V))^2}{4} - A \times T} \right\} \times \left\{ \frac{(T_p \times C_p)}{((T_p \times C_p) + (T_s \times C_s))} \right\}$$

where
$bA_p$ = Bound anti-ligand
$T_p$ = The number of ligands on $C_p$
$T_s$ = The number of ligands on $C_s$
$C_p$ = The number of target ligand constructs
$C_s$ = The number of subtractor ligand constructs
A = Total number of anti-ligand T=Total number of ligands
C=Avogadro's constant ($6.022 \times 10^{23}$ particles/mole)
V=Reaction volume (liters)
$K_d$=Equilibrium dissociation constant.

13. The method of claim 1 wherein said subtractor ligand construct and said target ligand construct each comprise a ligand associated with at least one of a solid support, cell membrane and/or portions thereof, synthetic membrane, beads, chemical tags and free ligand.

14. The method of claim 1 whereby the subtractor ligand construct and the target ligand construct have a different density.

15. The method of claim 1 wherein the subtractor ligand construct comprises a ligand associated with a membrane vesicle or a whole cell membrane.

16. The method of claim 1 whereby the isolation in sub-step (v) is performed by at least one of density centrifugation, solid support sequestration, magnetic bead sequestration, chemical tag binding and aqueous phase partitioning.

17. The method of claim 1 wherein the library of step (a) is a display library comprising a plurality of library members which display anti-ligands.

18. The method of claim 1 wherein the library is a phage display library.

19. The method of claim 1 wherein the ligand is at least one selected from antigens; receptor ligands; and enzyme targets that comprise at least one from carbohydrate; protein; peptide; lipid; polynucleotide; inorganic molecules and conjugated molecules.

20. The method of claim 1 wherein the anti-ligand library is constructed from at least one from antibodies, and antigen binding variants, derivatives or fragments thereof; scaffold molecules with engineered variable surfaces; receptors; and enzymes.

21. The method of claim 1 comprising a further step of exposing the subtractor ligand construct and the target ligand construct to a stimulus which influences the expression of target ligands on the subtractor ligand construct and the target ligand construct.

* * * * *